(12) United States Patent
Van Lintel et al.

(10) Patent No.: US 7,005,078 B2
(45) Date of Patent: Feb. 28, 2006

(54) MICROMACHINED FLUIDIC DEVICE AND METHOD FOR MAKING SAME

(75) Inventors: Harald T. Van Lintel, Lausanne (CH); Didier Maillefer, Belmont S/Lausanne (CH); Stephan Gamper, Pallaigues (CH)

(73) Assignee: Debiotech SA, Lausanne (CH)

( * ) Notice: Subject to any disclaimer, the term of this patent is extended or adjusted under 35 U.S.C. 154(b) by 123 days.

(21) Appl. No.: 10/296,466

(22) PCT Filed: May 25, 2001

(86) PCT No.: PCT/EP01/07032

§ 371 (c)(1),
(2), (4) Date: Mar. 31, 2003

(87) PCT Pub. No.: WO01/90577

PCT Pub. Date: Nov. 29, 2001

(65) Prior Publication Data

US 2004/0052657 A1     Mar. 18, 2004

(30) Foreign Application Priority Data

May 25, 2000  (FR) .................................. 00 06669

(51) Int. Cl.
*G01D 15/00* (2006.01)

(52) U.S. Cl. ........................ 216/27; 216/95; 438/52; 438/53; 438/745

(58) Field of Classification Search .................. 216/2, 216/27, 41, 56, 80, 97, 95; 438/21, 49, 51, 438/52, 53, 745
See application file for complete search history.

(56) References Cited

U.S. PATENT DOCUMENTS

| 6,069,392 | A | * | 5/2000 | Tai et al. ..................... 257/419 |
| 6,116,863 | A | * | 9/2000 | Ahn et al. ................... 417/322 |
| 6,596,545 | B1 | * | 7/2003 | Wagner et al. .............. 436/518 |

FOREIGN PATENT DOCUMENTS

| EP | 0483469 A1 | 8/1991 |
| EP | 0568902 A2 | 4/1993 |
| WO | WO 95/18307 | 7/1995 |
| WO | WO 97/29538 | 8/1997 |

OTHER PUBLICATIONS

Peter Gravesen, Jens Branebjerg and Ole Sondergard Jensen, "Microfluidics-a review," IOP Publishing Ltd. (United Kingdom), p. 168-182, (Jan. 30, 1993).

* cited by examiner

*Primary Examiner*—Lan Vinh
(74) *Attorney, Agent, or Firm*—Dennis G. LaPointe

(57) ABSTRACT

The fluid-flow device (100) of the invention comprises a stack (30) covered by a closure wafer (20), said stack (30) comprising a support wafer (36), a layer of insulating material (34), and a silicon layer (32). The closure wafer (20) and/or said silicon layer (32) are machined so as to define a cavity (38) between said closure wafer (20) and said silicon layer (32), said support wafer (36) has at least one duct (102) passing right through it, said layer of insulating material (34) presenting at least one zone (35) that is entirely free of material placed at least in line with said duct (102) so as to co-operate with said cavity (38) to define a moving member (40) in said silicon layer (32), the moving member (40) being suitable under the pressure of liquid in said cavity (38) for reversibly moving towards said support wafer (36) until contact is made between said moving member (40) and said support wafer (36).

17 Claims, 11 Drawing Sheets

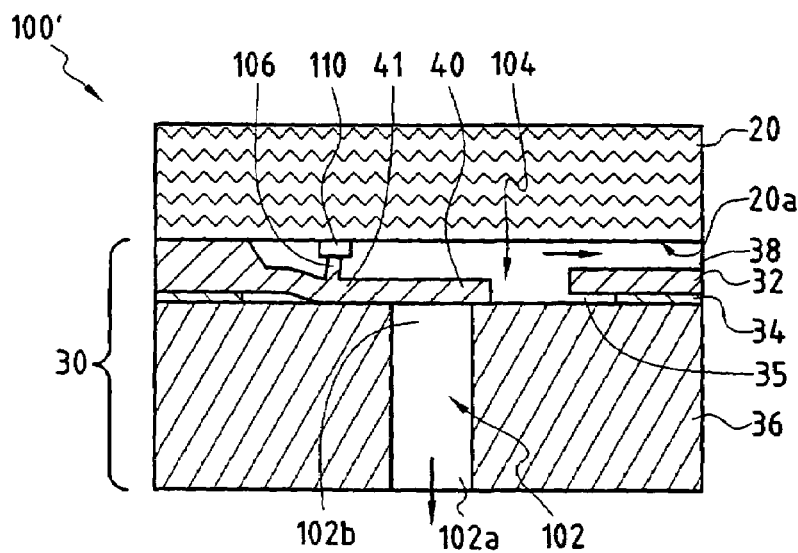
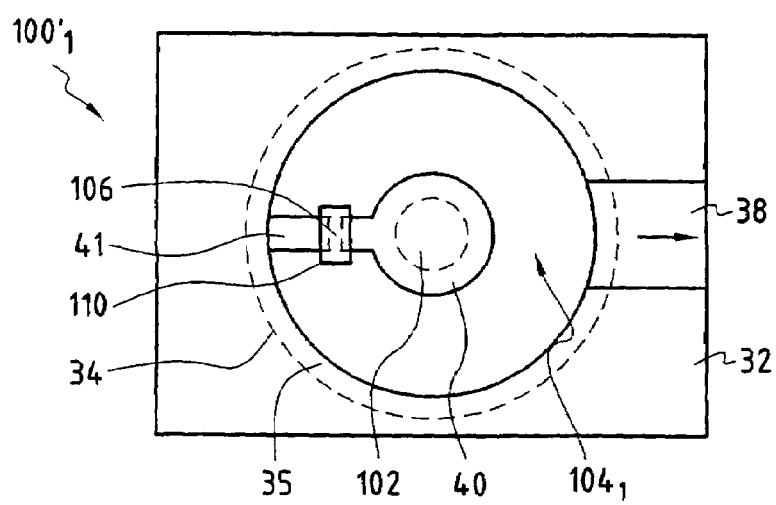
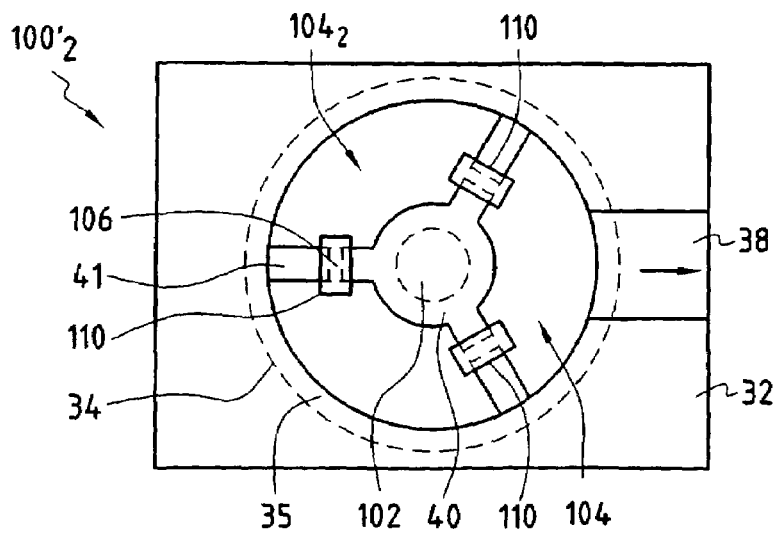

MICROMACHINED FLUIDIC DEVICE AND METHOD FOR MAKING SAME

The invention relates to a fluid-flow device and to its method of manufacture. The invention also relates to particular forms of fluid-flow device constituting a member for controlling liquid inlet, e.g. forming a non-return check valve, or a member for detecting liquid pressure.

The present invention also relates to a micropump constituting a fluid-flow device, and particularly but not exclusively forming a micropump for medical use for delivering a controlled quantity of a liquid medicine on a regular basis.

The manufacture of such fluid-flow devices, and in particular such micropumps is based on technologies for micromachining silicon or any other micromachinable material, in particular using photolithographic techniques with chemical etching, laser ablation, microreplication, etc.

For the particular above-specified application, and also in other cases, it is necessary to provide an inlet control member that allows the micropump to be self-priming. The micropump is driven by varying the volume of the pump chamber (alternately reducing it and increasing it), e.g. by delivering drive from a piezoelectric actuator.

The European patent application published under the No. 0 453 532 describes such a micropump. Nevertheless, such a micropump does not provide its own self-priming since it presents large dead volumes, these volumes contributing to degrading the compression ratio achieved by the micropump.

In order to improve that aspect, a novel micropump has been developed, such as that described in the international patent application published under the No. WO 99/09321. In order to minimize dead volumes and in particular dead volumes downstream from the seat of the inlet valve, an inlet valve is provided in that pump that is thick in that said inlet valve constitutes the entire thickness of an intermediate wafer (or intermediate plate), the seat of the valve being situated on its side opposite from the moving diaphragm (or membrane). Nevertheless, such a micropump is complex in structure, difficult to manufacture, and still has dead volumes that are large.

An object of the present invention is to provide a fluid-flow device, e.g. a member for controlling liquid inlet or a member for detecting liquid pressure or a micropump, capable of being manufactured in simplified manner and constituting a fluid-flow device that is made reliable in its operation by minimizing dead volumes.

To this end, the invention provides a fluid-flow device comprising a stack covered by a closure wafer (or closure plate), said stack comprising a support wafer (or support plate), a layer of insulating material covering at least part of said support wafer, and a layer of single-crystal or polycrystalline silicon covering said layer of insulating material and covered by said closure wafer, said closure wafer and/or said silicon layer being machined so as to define between said closure wafer and said silicon layer a cavity to be filled with liquid, said support wafer having at least one duct passing right through it, and said layer of insulating material having at least one zone that is entirely free from material placed at least in line with said duct so as to co-operate with said cavity to define a moving member in said silicon layer that responds to pressure of the liquid in said cavity by moving reversibly towards said support wafer. In a first type of fluid-flow device, said moving member moves reversibly towards said support wafer until making contact between said moving member and said support wafer.

According to preferred characteristics:

said support wafer is made of silicon, of quartz, or of sapphire, and presents thickness lying in the range 50 micrometers ($\mu$m) to 1 millimeter (mm), and preferably in the range 300 $\mu$m to 500 $\mu$m;

said layer of insulating material is of thickness lying in the range 100 nanometers (nm) to 2 $\mu$m, and preferably in the range 0.5 $\mu$m to 1 $\mu$m;

said closure wafer is made of glass or of silicon, preferably single-crystal silicon; and said layer of silicon is made of single-crystal or polycrystalline silicon and presents thickness lying in the range 1 $\mu$m to 100 $\mu$m, and preferably in the range 10 $\mu$m to 50 $\mu$m.

In another aspect, the present invention provides a method of manufacturing a fluid-flow device of the above-specified type, the method being characterized in that it comprises the following steps:

providing a stack comprising a support wafer, a layer of insulating material, preferably made of silicon oxide, covering at least part of said support wafer, and a layer of single-crystal or polycrystalline silicon covering said layer of insulating material and presenting a free face;

using photolithography and chemical etching to machine said cavity from said closure wafer and/or from the free face of said silicon layer;

using photolithography and chemical etching to machine at least one duct passing right through said support wafer;

chemically etching said layer of insulating material at least via said duct such that a zone of said silicon layer is freed from said layer of insulating material, thereby forming said moving member;

providing at least one closure wafer; and using a physicochemical method, preferably by wafer bonding, to connect said closure wafer in leaktight manner to said surface of silicon layer that has not been machined.

Thus, in the present invention, it is preferable to use a stack comprising a silicon support wafer covered in a layer of silicon oxide, itself covered in a layer of silicon. The stack is commercially available and is conventionally referred to as silicon-on-insulator (SOI).

The use of this type of stack makes it possible to obtain a fluid-flow device presenting thicknesses that are constant and under strict control, while nevertheless implementing a method of manufacture that is simple.

In particular, this method of manufacture is considerably simpler to implement than the method described in the international patent application published under No. WO 98/14704.

The various portions of the fluid-flow device are made by selective chemical etching from both sides of the stack, i.e. from both faces of the wafer constituting said stack: the layer of insulating material (made of silicon oxide in an SOI stack) forms a stop or a barrier against etching during micromachining of the support wafer or of the silicon layer.

In addition, the closure wafer, which serves to close in particular the cavity made in the machined silicon layer, is itself preferably made of glass or of single-crystal silicon.

When the closure wafer is made of glass, it is fixed to the layer of silicon in a manner that is known per se, using the technique of anodic bonding.

When the closure wafer is made of silicon, it is fixed to the silicon layer using the known direct Si—Si bonding technique.

In a first aspect of the fluid-flow device of the invention, there is provided a liquid inlet control member forming a non-return check valve, the member comprising a stack covered in a closure wafer, said stack comprising a support wafer, preferably made of silicon, a layer of insulating material, preferably made of silicon oxide, covering at least part of said support wafer, and a layer of single-crystal or polycrystalline silicon covering said layer of insulating material and covered by said closure wafer, said closure wafer and/or said silicon layer being machined so as to define a cavity between said closure wafer and said silicon layer, said cavity being designed to be filled with liquid and presenting at least one gap (or clearance hole) machined in the entire thickness of the silicon layer, said support wafer having at least one liquid inlet duct passing right through it and situated at least in register with (facing) said cavity, and said layer of insulating material having at least one zone entirely free of material extending at least in line with said duct and said gap so as to co-operate with said cavity to define a moving member in said silicon layer to form a flap for said valve, a portion of said silicon layer surrounding said moving member presenting elasticity making it possible in the event of a difference in liquid pressure between said liquid inlet duct and said cavity to allow said moving member to move reversibly towards said support wafer.

In this first type of fluid-flow device, said liquid inlet duct of the liquid inlet control member defined in the preceding paragraph is situated close to but not in register with said gap, and said moving member moves between a closed position in which the moving member is in leaktight contact against said support wafer which forms a seat for said valve at least around said duct, liquid flow being prevented between said liquid inlet duct and the cavity, and an open position of the valve in which the moving member is no longer in leaktight contact against the support wafer around said duct, in which the moving member allows liquid flow from said liquid inlet duct towards said gap.

In a second aspect of the fluid-flow device of the present invention, there is provided a liquid pressure detection member comprising a stack covering a closure wafer, said stack comprising a support wafer, preferably made of silicon, a layer of insulating material, preferably made of silicon oxide, covering at least part of said support wafer, and a layer of single-crystal or polycrystalline silicon covering said layer of insulating material and covered by said closure wafer, said closure wafer and/or said silicon layer being machined so as to define a cavity for filling with liquid between said closure wafer and said silicon layer, said support wafer having as least one duct passing right through it and situated in register with (facing) said cavity, and said layer of insulating material having at least one zone that is entirely free of material placed at least in line with said duct so as to co-operate with said cavity to define a moving member in said layer of silicon, said silicon support wafer presenting a portion in register with (facing) the moving member forming an island that is separated from the remainder of the support wafer by said duct, said moving member being capable, by virtue of its elasticity and under pressure of liquid in said cavity, of moving reversibly towards the support wafer.

In the first type of fluid-flow device, said moving member of the liquid pressure detection member as defined in the preceding paragraph is capable of going from an open position to a closed position in which the moving member is in physical contact with said portion situated facing the moving member forming an island that is separated from the remainder of the support wafer by said duct and which forms a bearing portion of the silicon wafer, said physical contact being electrically detectable.

In a third aspect of the fluid-flow device of the present invention, there is also provided a micropump comprising a stack covered in a closure wafer, said stack comprising a support wafer, preferably made of silicon, a layer of insulating material, preferably made of silicon oxide, covering at least part of said support wafer, and a layer of single-crystal or polycrystalline silicon covering said layer of insulating material and covered by said closure wafer, said closure wafer and/or said silicon layer being machined so as to define a cavity between said closure wafer and said silicon layer, the cavity being for filling with liquid and including a pump chamber, said support wafer comprising at least a first duct passing right through it and situated in register with (facing) said cavity, said layer of insulating material having at least one first zone that is entirely free of material placed at least in line with said first duct so as to co-operate with said cavity to define a first moving member in said silicon layer, the first moving member being suitable under pressure of liquid in said pump chamber for moving reversibly towards said support wafer, said first moving member forming part of the flap of a liquid inlet control member, and said micropump further comprising a pumping portion comprising control means fitted with a pump diaphragm to cause the volume of the pump chamber to vary periodically, and liquid outlet control means.

In the first type of fluid-flow device, the first moving member of the liquid inlet control member defined in the preceding paragraph is suitable, under the pressure of the liquid in said pump chamber, for coming into leaktight contact against said support wafer, said first moving member constituting the flap of said liquid inlet control member.

In preferred manner, said micropump further comprises a second zone, in the layer of insulating material, that is entirely free of material which co-operates with said cavity to define a second moving member in said silicon layer, the second moving member being suitable under the pressure of liquid in said pump chamber for moving towards said support wafer, said second moving member constituting the flap of a liquid outlet control member.

Thus, the present invention relates to various types of fluid-flow device which, in accordance with the essential characteristic of the present invention, are made form a stack of the SOI type, i.e. comprising a support wafer that is preferably made of silicon, covered in layer of insulating material, preferably silicon oxide, itself covered in a layer of silicon.

Thus, contrary to prior art fluid-flow devices and micropumps for which it is necessary to perform machining throughout the thickness of a silicon wafer that is to form the intermediate wafer between two wafers of glass, the present invention proposes using a stack in which the initial thicknesses of the three components (support wafer, layer of insulating material, and silicon layer) serve firstly to ensure that the various portions of the fluid-flow device are of well-controlled thickness, and secondly that the dead volumes are very considerably reduced compared with the prior art.

Another major advantage of the technology of the present invention lies in the manufacturing method being simplified compared with the techniques of the prior art.

The invention will be better understood and secondary characteristics and advantages thereof will appear on reading the following description of various embodiments of the invention given by way of example.

Naturally the description and the drawings are given purely by way of non-limiting indication.

Reference is made to the accompanying drawings, in which.

Figure 1:
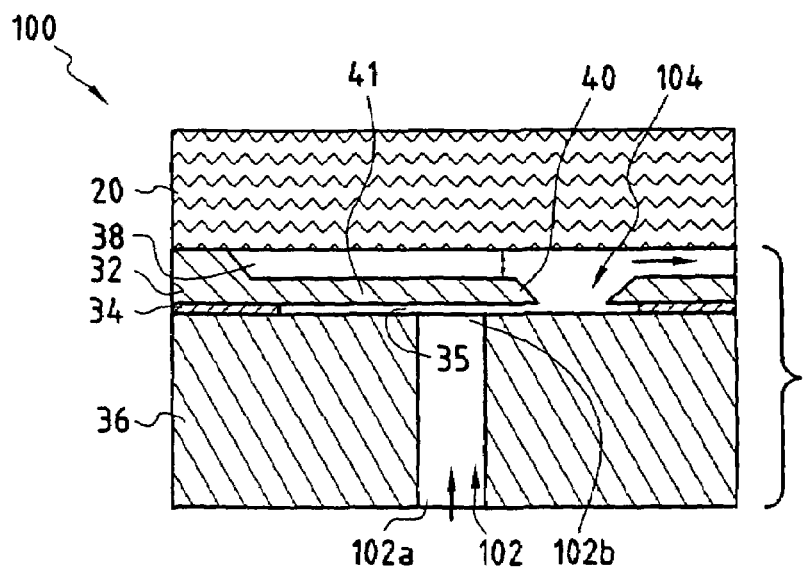
FIG. 1 is a cross-section through a liquid inlet control member, constituting a first aspect of a fluid-flow device of the present invention, implementing a first embodiment thereof.
Figure 1A:
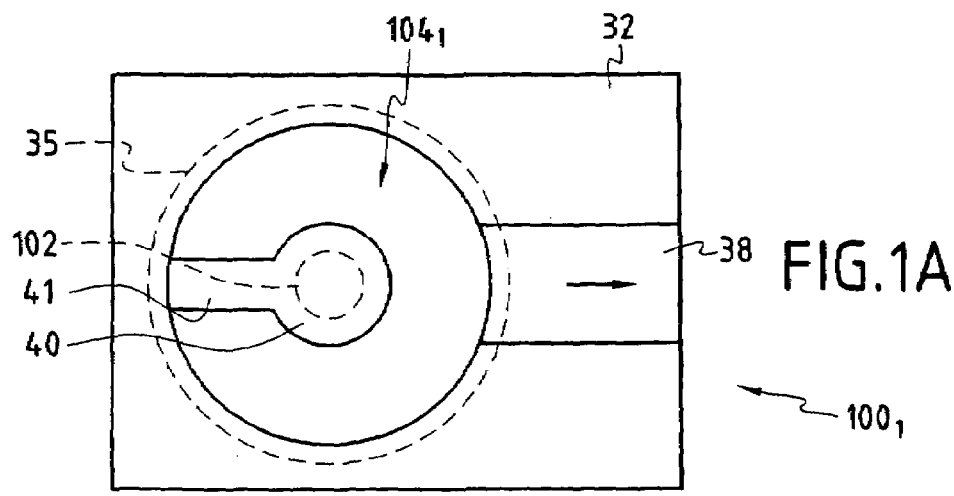
FIGS. 1A and 1B are plan views of two variants of the FIG. 1 liquid inlet control member, the closure wafer covering the stack being removed.
Figure 1B:
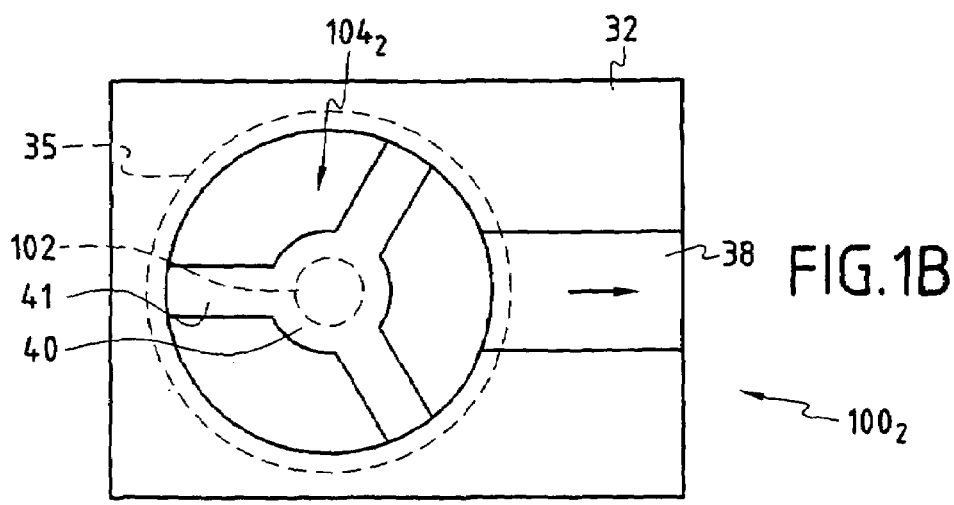
Figure 3:
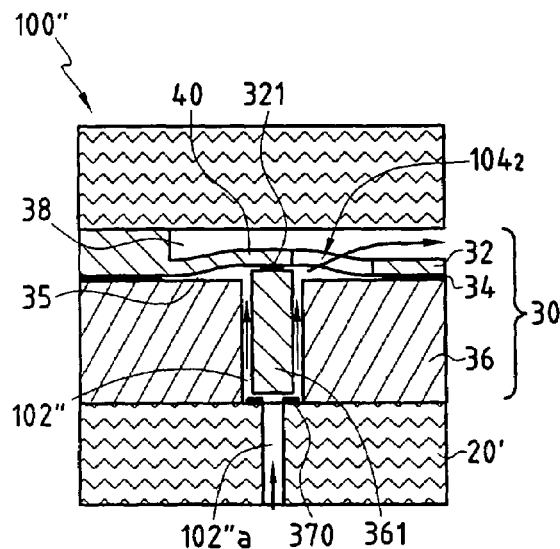
Figure 4:
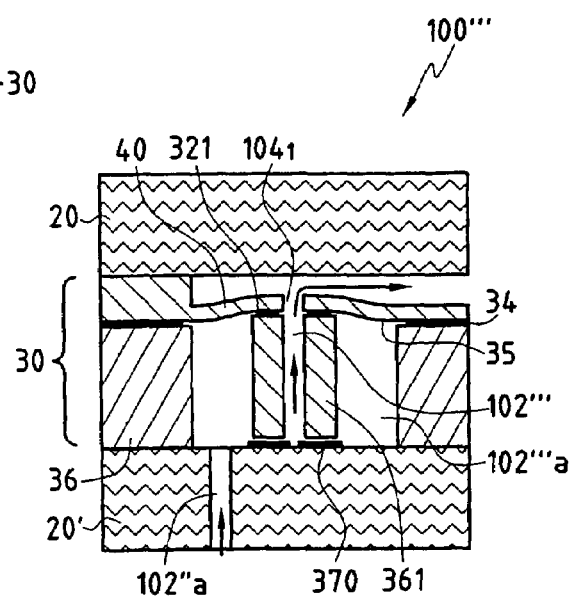
Figure 3A:
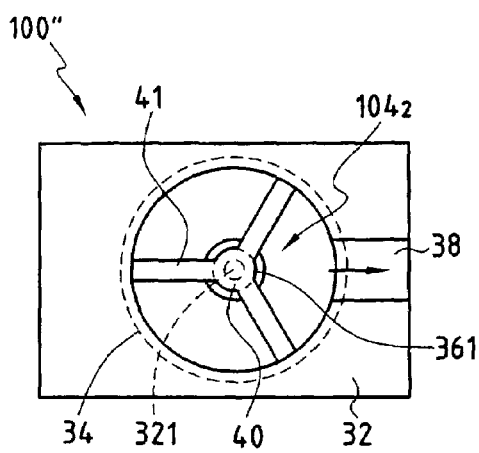
Figure 4A:
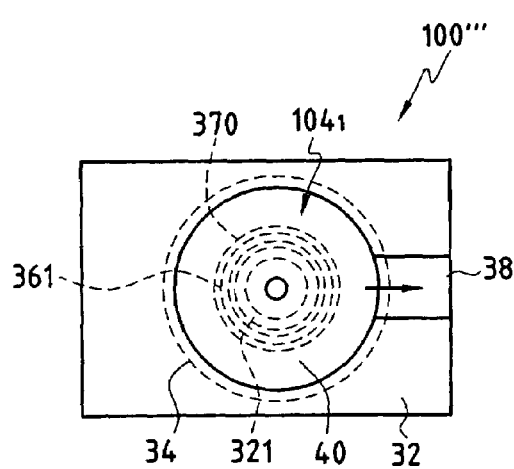
Figure 5:
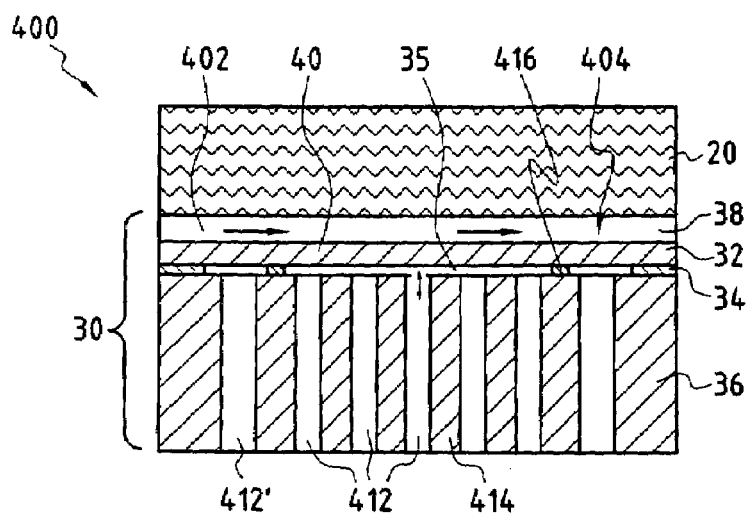
Figure 5A:
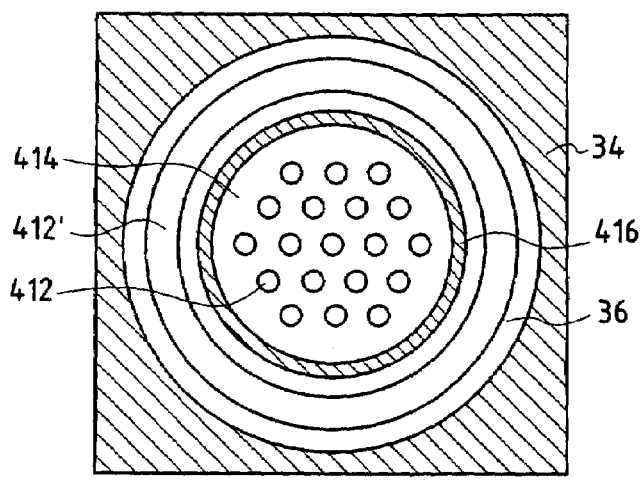
Figure 5B:
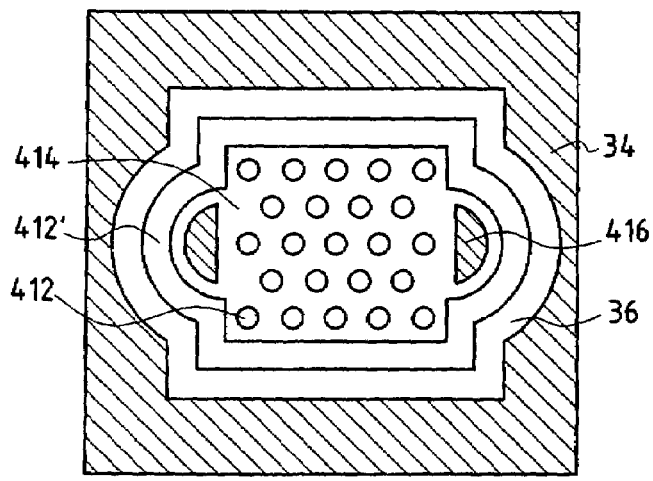
Figure 6:
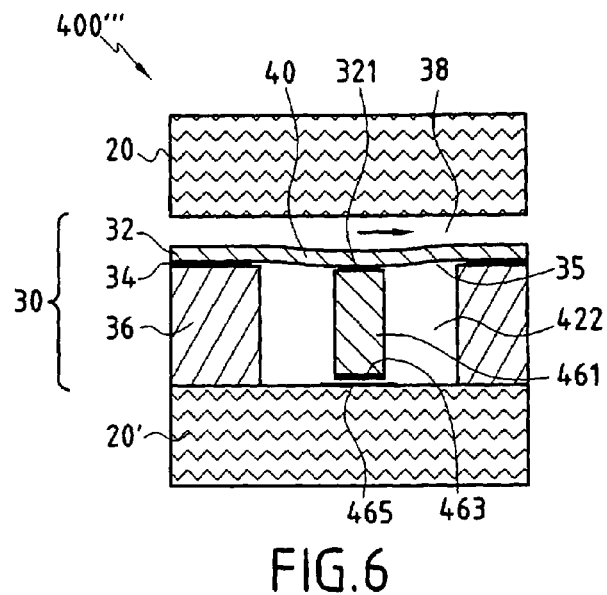
Figure 8:
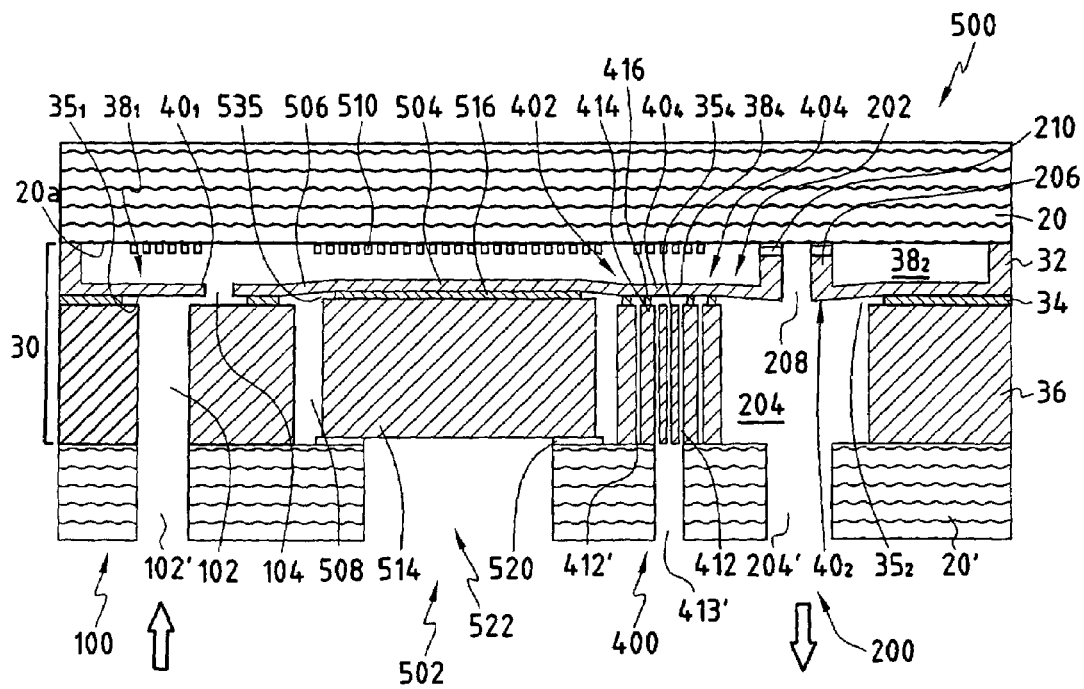
Figure 7:
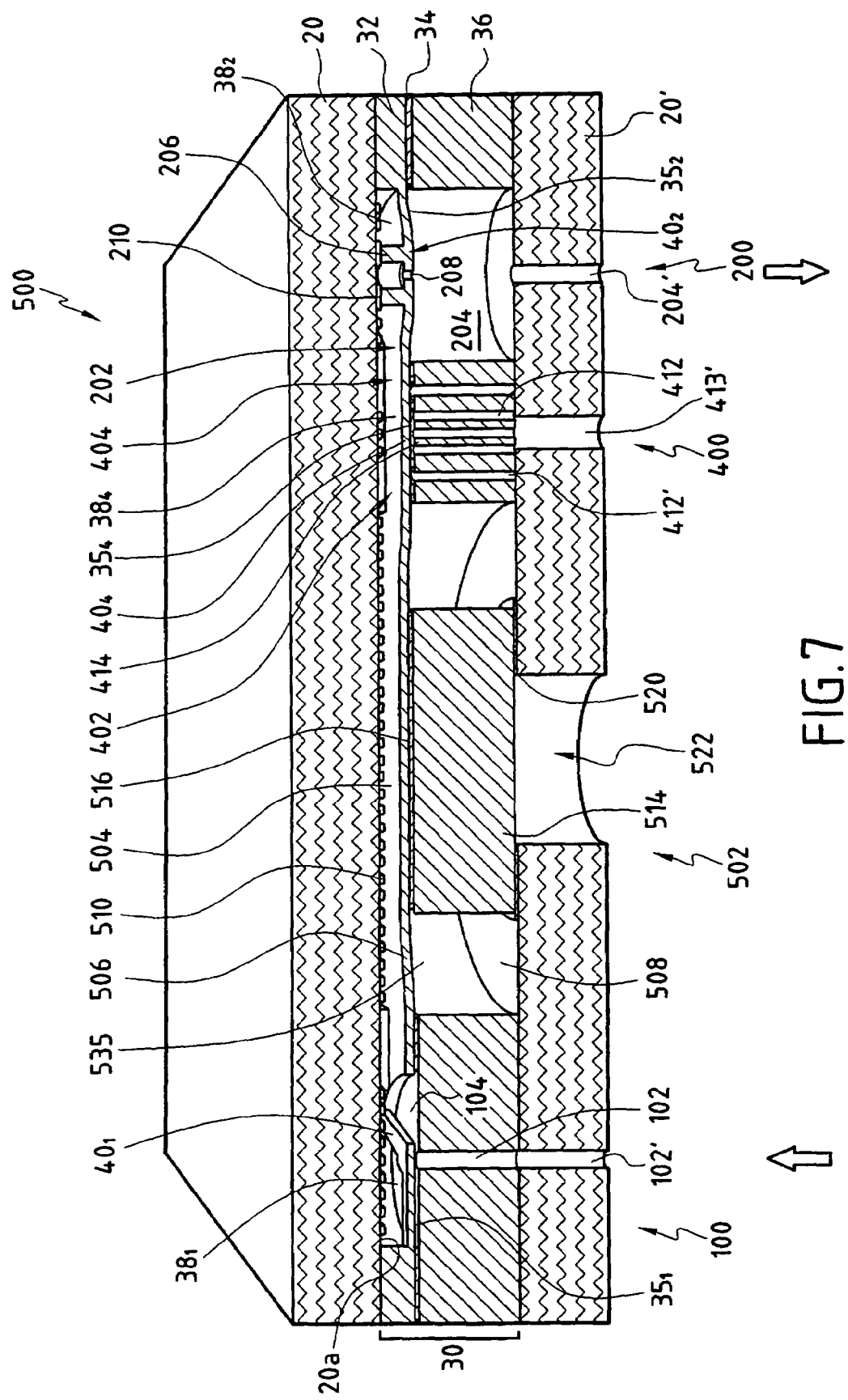
Figure 9:
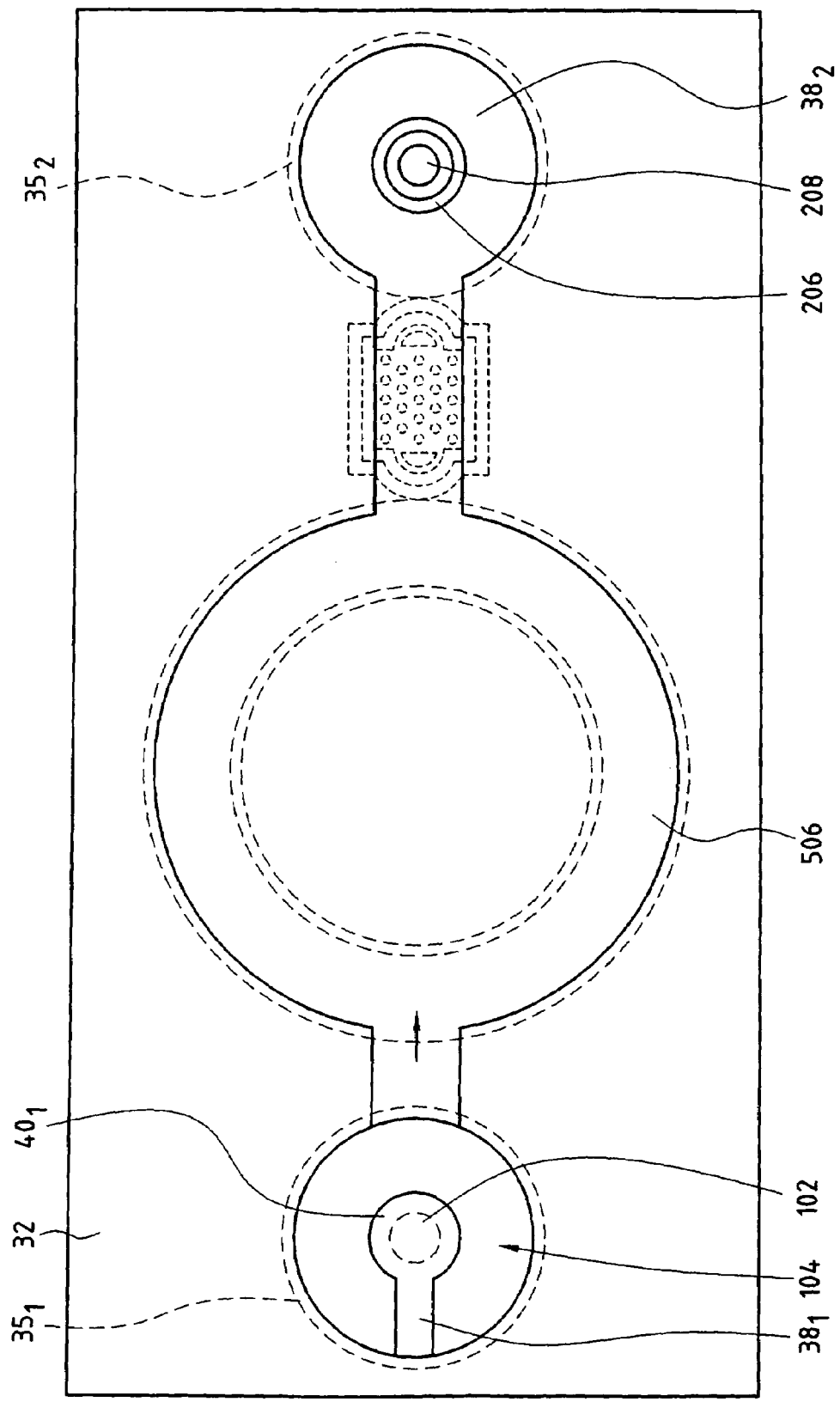
Figure 10:
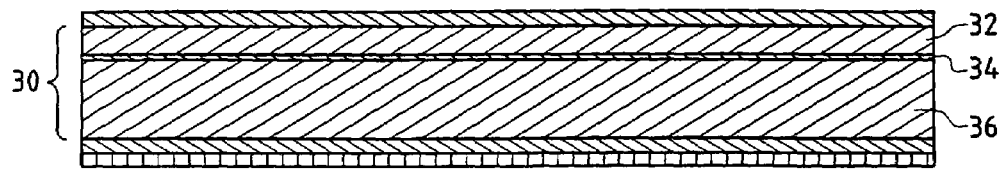
Figure 16A:
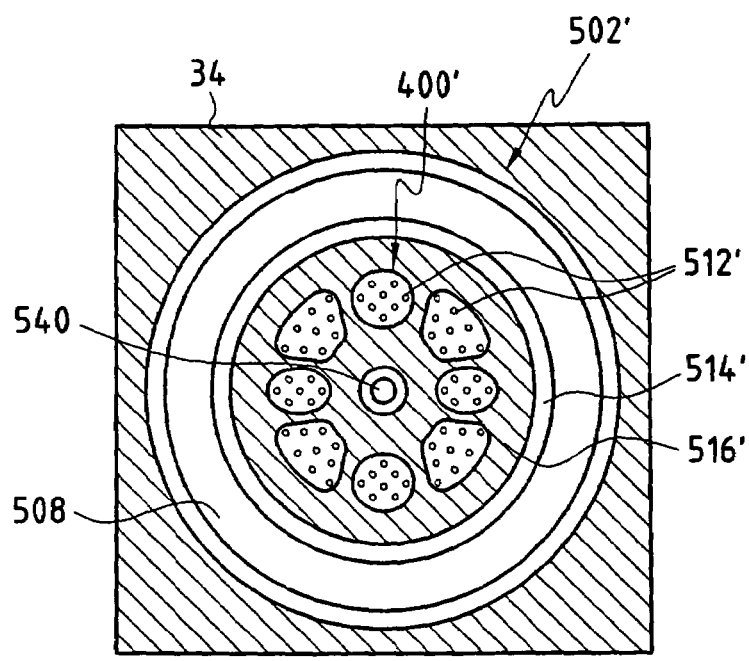
Figure 16B:
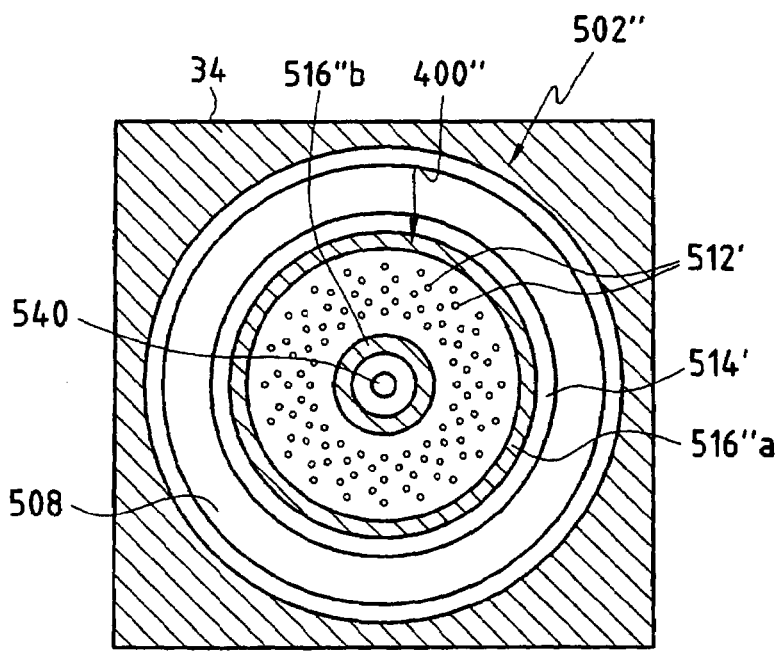
Figure 17:
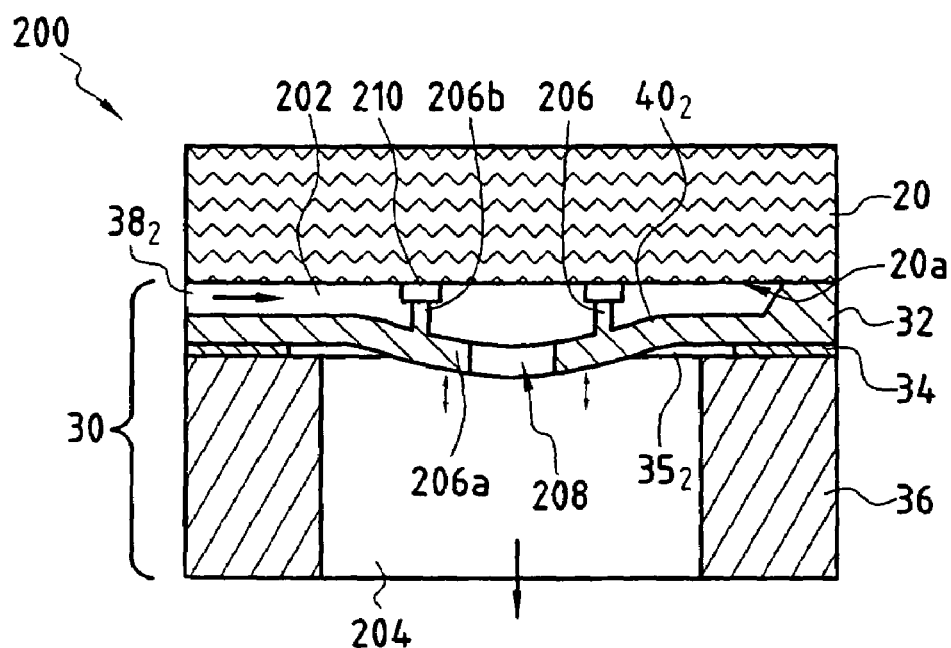
Figure 18:
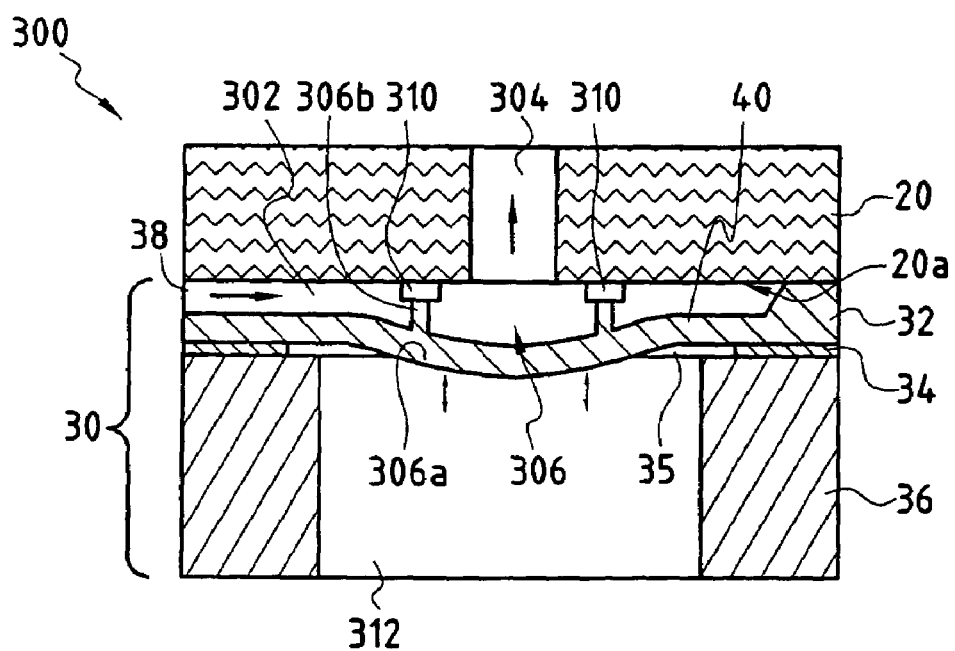

FIGS. 2, 2A, and 2B are views similar to those of FIGS. 1, 1A, and 1B, showing a second embodiment of the first aspect of a fluid-flow device of the present invention;

FIGS. 3 and 3A are views similar to FIGS. 1 and 1A showing a third embodiment of the first aspect of a fluid-flow device of the present invention;

FIGS. 4 and 4A are views similar to FIGS. 1 and 1A showing a fourth embodiment of the first aspect of a fluid-flow device of the present invention;

FIG. 5 is a cross-section through a liquid pressure detector constituting a second aspect of a fluid-flow device of the present invention;

FIGS. 5A and 5B are plan views of two variant embodiments of the FIG. 5 liquid pressure detector, the closure wafer covering the stack and the silicon layer being removed;

FIG. 6 is a view similar to FIG. 5 showing a second embodiment of the second aspect of a fluid-flow device of the present invention;

FIG. 7 is a longitudinal section view, partially in perspective, of a micropump constituting a third aspect of a fluid-flow device of the present invention;

FIG. 8 is a diagrammatic longitudinal section view of the FIG. 7 micropump;

FIG. 9 is a plan view of the micropump of FIGS. 7 and 8, the closure wafer covering the stack being removed;

FIGS. 10 to 15 show various steps in the manufacture of the pump of FIGS. 7 and 8;

FIG. 16A is a plan view of a variant embodiment of the pumping portion of FIGS. 7 to 9, forming a plurality of liquid pressure detectors, the closure wafer covering the stack and the silicon layer being removed;

FIG. 16B is a view similar to FIG. 16A showing another variant embodiment of the pumping portion of FIGS. 7 to 9, forming a liquid pressure detector of angular shape;

FIG. 17 is a view on a larger scale of the liquid outlet control member of the micropump of FIGS. 7 and 8; and FIG. 18 shows a variant embodiment of the liquid outlet control member of FIG. 17.

Throughout the figures, when the same element is shown in a plurality of figures it is always given the same numerical reference.

In addition, for reasons of clarity, it should be understood that the thickness of the various elements shown are exaggerated to a very great extent in the drawings so that the drawings are not strictly to scale.

In a first aspect of the fluid-flow device of the present invention, the fluid-flow device forms a liquid inlet control member and an embodiment thereof is shown in FIG. 1. This liquid inlet control member 100 for constituting a one-way valve or check valve (non-return valve) comprises a glass closure wafer 20 placed on top of a stack 30 that has previously been machined in order to form the various functional portions of said control member 100.

The stack 30 comprises a silicon layer 32 surmounting a silicon oxide layer 34, itself placed on a silicon support wafer 36.

This type of stack is commonly referred to as a silicon-on-insulator (SOI) stack and is commercially available in the form of wafers or plates suitable for use in the semiconductor electronics industry. The roles of these three elements in the stack 30 determine thicknesses that are significantly different:

- the silicon support wafer 36 acting as a rigid base preferably has thickness lying in the range 50 $\mu$m to 1000 $\mu$m, and advantageously in the range 300 $\mu$m to 500 $\mu$m;
- the silicon oxide layer 34 serves to connect the silicon support wafer 36 to the silicon layer 32 while maintaining a constant spacing between them, and while also being easy to remove in certain zones so its thickness should remain very small, preferably lying in the range 0.1 $\mu$m to 2 $\mu$m, and advantageously in the range 0.5 $\mu$m to 1 $\mu$m; and
- the silicon layer 32 is designed to be machined throughout its thickness to form liquid passages or through a fraction only of its thickness (about half) so as to co-operate with the glass closure wafer 20 to define a cavity, and in some cases a moving member; this silicon layer 32 which may be made of single-crystal or polycrystalline silicon, presents initial thickness that lies preferably in the range 1 $\mu$m to 100 $\mu$m, and advantageously in the range 10 $\mu$m to 50 $\mu$m.

The stack 30 is machined by conventional techniques of photolithography and chemical etching in order to obtain the various functional elements of the inlet control member 100, in particular a cavity 38 and a moving member 40, prior to connecting the glass closure wafer 20 with said stack 30. This connection between the closure wafer 20 and the free face of the silicon layer 32 is performed in known manner by wafer bonding (anodic bonding when the closure wafer is made of glass) serving to produce fixing that constitutes a leaktight connection.

A liquid inlet duct 102 passes through the silicon support wafer going right through its entire thickness from a first end 102a to a second end 102b. The second end 102b is adjacent to a circular zone 35 of the silicon oxide layer 34 that is completely free from material and that extends well beyond the liquid inlet duct 102.

The silicon layer 32 has been machined through a fraction of its thickness on its side remote from the silicon support wafer 36 so as to form the cavity 38. In addition, a gap 104 (or clearance hole) corresponding to the entire thickness of the silicon layer 32 being removed is situated in line with the cavity 38 and the zone 35 having no silicon oxide, close to but not directly in register with (facing) the second end 102b of the liquid inlet duct 102 which faces towards the silicon oxide layer 34.

The cavity 38 extends in register with at least said zone 35 and the liquid inlet duct 102.

In this manner, as can be seen more clearly in FIGS. 1A and 1B, there is formed a member 40 in the silicon layer 32, said member 40 not being connected to the glass closure wafer 20, nor to the silicon oxide layer 34, with said member 40 being separated from the remainder of the silicon layer 32 by the gap 104.

In a first variant embodiment, the liquid inlet control member $100_1$ shown in FIG. 1A has a gap $104_1$ in the form of an open ring such that the moving member is connected to the remainder of the silicon layer 32 by an arm 41 situated to the left in FIG. 1A.

In a second variant embodiment, the liquid inlet control member $100_2$ shown in FIG. 1B comprises a gap $104_2$ in the form of three angular sectors subtending an angle at the center of about 120° so that the moving member is connected to the remainder of the silicon layer 32 by three arms 41 each situated between two of the above-mentioned angular sectors.

It will be understood that the member 40 is movable in a direction perpendicular to the main plane of the stack 30, i.e. upwards in FIG. 1, and orthogonally to the plane of the sheet in FIGS. 1A and 1B. Nevertheless, in the second variant embodiment, because of the three points attaching the moving member 40 to the silicon layer 32, it will be understood that the moving member 40 is stiffer than it is in the first variant embodiment.

The very small thickness of this member 40 (less than 50 $\mu$m, and preferably about 10 $\mu$m) makes it elastically movable in a direction extending transversely to the main plane of the stack 30 or of the glass closure wafer 20, i.e. up and down as represented by the double-headed arrow in FIG. 1.

In FIG. 1, the member 100 forming an inlet valve is shown in its rest position, i.e. partially open. When liquid arrives via the inlet duct 102, the moving member 40 lifts under the pressure of the liquid which is then higher in the inlet duct 102 than in the cavity 38, such that the valve takes up its open position and enables the liquid to penetrate into the zone 35, and to pass into the gap 104 so as to reach the cavity 38.

This member 100 can be inserted in a fluid-flow assembly that is more complex, in which the member 100 constitutes an upstream liquid inlet element. Thus, it will be understood that the liquid present in the cavity 38 can be at a pressure which is higher than the pressure of the liquid in the inlet duct 102, thus enabling the member 100 to close by the moving member moving downwards and coming into leaktight contact against the face of the silicon support wafer 36 facing towards the silicon layer all around the second end 102b of the duct 102.

The relative elasticity of the silicon layer 32 that is thinned-down in the location of the cavity 38 (a single arm 41 in FIG. 1A, or three arms 41 in FIG. 1B), makes it possible when the pressure of the liquid in the cavity 38 is no longer greater than the pressure of the liquid in the duct 102 for the member 40 to return to its initial position as shown in FIG. 1, i.e. a position in which the member 100 is partially closed. When the pressure of the liquid in the cavity 38 becomes higher than the pressure of the liquid in the duct 102, then the moving member 40 moves fully down and comes into leaktight contact against the support wafer 36: the liquid inlet control member 100 is then closed.

It will be understood that this member 100 forms an inlet valve in which the valve body is constituted by the face of the moving member 40 facing towards the silicon support wafer 36 and in which the seat of the valve is constituted by the region of the face of the silicon support wafer 36 that faces towards the silicon layer 32 surrounding the second end 102b of the duct 102.

In a second embodiment shown in FIGS. 2, 2A, and 2B, it is also possible to establish prestress placing the liquid inlet control member 100' in its closed position when the moving member 40 is in its rest position.

For this purpose, an isolated portion 106 of the moving member 40, situated in the middle of the arm 41, is of a thickness that is equal to the initial thickness of the silicon layer 32. This portion 106 lies in register with an element 110 situated on the face 20a of the closure wafer 20 facing towards the stack, or on the free face of said portion 106.

The element 110 is preferably taken from a layer of titanium deposited on the above-specified face 20a of the closure wafer 20. This element 110 pushes the isolated portion 106 downwards and forces the moving member 40 into its closed position which then corresponds to its rest position. Nevertheless, the elasticity of the moving member 40 remains sufficient to enable it to be opened.

Thus, the portion 106 and said element 110 form bearing means placing said moving member 40, when in its rest position, in said closed position.

FIGS. 3 and 3A relate to a third embodiment of the liquid inlet control member constituting the first aspect of the invention. In this case, the liquid inlet control member 100" further comprises, compared with the first and second embodiments of the liquid inlet control member, a second glass wafer 20'.

Thus, in this liquid inlet control member 100, the top closure wafer 20 is a first closure wafer 20 of glass and the second glass wafer 20' forms a second closure wafer which is fixed to the face of the support wafer 36 opposite from said first glass closure wafer 20.

This second closure wafer 20' of glass is provided with a through duct 102"a.

To move the body and the seat of the valve between the second closure wafer 20' and the silicon support wafer 36, a moving portion 361 is formed throughout the thickness of the support wafer 36 in register with and in line with said cavity 38 of said moving member 40 and of said duct 102"a. This moving portion 361 is situated close to but not in register with said gap 104$_2$.

A matter-free annular volume 102" is machined through the entire thickness of the support wafer 36 in register with said zone 35 that is entirely free from material in the layer of insulating material 34, thereby separating said moving portion 361 from the remainder of the support wafer 36 and thus forming said liquid inlet duct 102" of the support wafer 36 which communicates with said gap 104$_2$.

The layer of insulating material 34 presents a connection zone 321 surrounded by the zone 35 which is then annular, the connection zone 321 securely connecting said moving portion 361 to said moving member 40, thus subjecting the moving portion 361 to the up or down movement of the moving member 40.

An annular valve element 370 made in an anti-adhesion material (preferably titanium) is situated on the face of the second closure wafer 20' made of glass placed in register with said moving portion 361.

Because of this valve element 370, when said moving member 40 is as close as possible to the support wafer 36 (a situation that is not shown), the face of the moving portion 361 facing towards the second closure wafer 20' and the face of the valve element 370 facing towards the support wafer 36 are in leaktight contact, thus putting the liquid inlet control member 100" into its closed position and preventing liquid from passing from the duct 102"a of the second closure wafer 20' towards said liquid inlet duct 102" of the support wafer 36.

In contrast, when there is no contact between the valve body (moving portion 361 in the example shown in FIGS. 3 and 3A) and the seat of the valve (valve element 370 in the example shown in FIGS. 3 and 3A), then the liquid inlet control member 100" is in its open position allowing liquid to pass from the duct 102"a of the second closure wafer 20' towards said liquid inlet duct 102" of the support wafer 36, and from there towards the gap 104$_2$ and onto the cavity 38. This is the situation shown in FIG. 3.

With reference to FIG. 3A, there can be seen the liquid inlet control member 100" of FIG. 3 in plan view after the closure wafer 20 has been removed, and it can be seen that there is a high degree of similarity with FIG. 1B since the moving member 40 is likewise connected by three arms 41 to the remainder of the silicon layer 32. The gap 104$_2$ is thus likewise made up of three angular sectors each subtending an angle at the center of about 120°, which sectors are annular in this case.

FIGS. 4 and 4A relate to a fourth embodiment of the liquid inlet control member constituting the second aspect of the invention. In this case, as for the third embodiment shown in FIGS. 3 and 3A, the liquid inlet control member 100''' further comprises a second glass wafer 20', as compared with the first and second embodiments of the liquid inlet control member.

This second glass wafer 20' forms a second glass closure wafer which is fixed to the face of the support wafer 36 opposite from said first glass closure wafer 20 and provided with a duct 102"*a* passing right through it.

Like in the third embodiment of the liquid inlet control member as shown in FIGS. 3 and 3A, and likewise for the purpose of offsetting the body and the seat of the valve between the second closure wafer 20' and the silicon support wafer, a moving portion 361 is made throughout the thickness of the support wafer 36 of the liquid inlet control member 100''', in register with and in line with said cavity 38 and said moving member 40.

This moving portion 361 is annular (see FIGS. 4 and 4A) and it is initially defined by a first annular volume 102'''*a* that has no material and that has been machined throughout the thickness of the support wafer 36 in register with said zone 35 that is completely free from material in the layer of insulating material 34 and said cavity 38. Thus, the first annular volume 102'''*a* separates said moving portion 361 from the remainder of the support wafer 36.

This annular moving portion 361 is subsequently likewise defined by a second cylindrical volume 102''' which is free from material and which is machined through the entire thickness of the support wafer 36 at the location (middle) of the moving portion 361. This second material-free volume 102''' forms said liquid inlet duct 102''' which communicates with the gap 104$_1$ which is then situated in register with and in line with said liquid inlet duct 102'''.

Also in the same manner as for the third embodiment of the liquid inlet control member 100" shown in FIGS. 3 and 3A, the layer of insulating material 34 of the liquid inlet control member 100''' of this fourth embodiment presents a connection zone 321 surrounded by the zone 35 and connecting said moving portion 361 securely to said moving member 40 around the liquid inlet duct 102''' and the gap 104$_1$. In this case, the connection zone 321 and the zone 35 are annular and concentric.

This liquid inlet control member 100''' further comprises an annular valve element 370 made of an anti-adhesion material (preferably titanium) situated on the face of the second glass closure wafer 20' placed facing said moving portion 361.

This annular valve element 370 surrounds said liquid inlet duct 102''' of the support wafer 36, but does not surround the duct 102"*a* of the closure wafer 20' which opens out into the first annular volume 102'''*a* that is free from material in the support wafer 36.

Because of this valve element 370, when said moving member 40 is as close as possible to the support wafer 36 (a situation which is not shown), the face of the moving portion 361 facing towards the second closure wafer 20' and the face of the valve element 370 facing towards the support wafer 36 are in leaktight contact, thus putting the liquid inlet control member in its closed position. In this closed position of the liquid inlet control member 100''', the liquid reaching the first annular volume 102''' from the duct 102"*a* of the second closure wafer 20' cannot penetrate into said liquid inlet duct 102''' of the support wafer 36: the liquid remains blocked in the first annular volume 102'''*a* of the support wafer 36.

In contrast, when there is no contact between the valve body (the moving portion 361 in the example shown in FIGS. 4 and 4A), and the valve seat (the valve element 370 in the example shown in FIGS. 4 and 4A), then the liquid inlet control member 100''' is in its open position (see FIGS. 4 and 4A) allowing liquid to pass from the duct 102"*a* of the second closure wafer 20' towards the first annular volume 102'''*a* of the support wafer 36, and then between the moving portion 361 and the valve element 370 towards the liquid inlet duct 102''' of the support wafer 36, and then towards the gap 104$_1$ heading towards the cavity 38.

The valve elements 370 in the third and fourth embodiments of the liquid inlet control member (100" and 100''') could equally well be situated on the face of said moving portion 361 that is placed facing the second glass closure wafer 20' and/or could equally well be made of some other anti-adhesion material such as gold, silicon oxide, or silicon nitride.

Thus, the third and fourth embodiments of the liquid inlet control member as shown respectively in FIGS. 3 & 3A and 4 & 4A belong to a second type of fluid-flow device in which a second glass wafer 20' is needed to offset the valve seat between said second glass wafer 20' and a moving portion 361 of the support wafer 36 of the stack 30.

The operation of the liquid inlet control members 100" and 100''' is identical to that of the liquid inlet control members 100 and 100' constituting the first and second embodiments (respectively shown in FIGS. 1, 1A, 1B, and in FIGS. 2, 2A, and 2B).

Compared with the method of manufacturing the liquid inlet control members 100 and 100' of the first and second embodiments (as shown respectively in FIGS. 1, 1A, 1B, and FIGS. 2, 2A, and 2B), in order to manufacture liquid inlet control members 100" or 100''' it suffices to provide a second closure wafer 20' on which an annular valve element 370 is deposited, said valve element being made of an anti-adhesion material, and then to connect it to the silicon wafer 36. These two steps should be performed at the end of the manufacturing method, i.e. after the stack 30 has been subjected to treatment (in particular by machining and/or structuring).

The presence of the valve element 370 in the liquid inlet control members 100' or 100''' makes it possible to subject the moving member 40 to pretension, since the presence of the thickness of the valve element 370 offsets the moving member 40 a corresponding distance upwards (see FIGS. 3 and 4) into the cavity 38.

Because of the micromachining techniques that can be used for processing the stack 30, it is possible to control the volumes of the liquid inlet ducts 102" or 102''' of the support wafer 36 very accurately in order to minimize the dead volume represented by said ducts.

The liquid inlet control members 100" or 100''' as described above can be integrated in a micropump as described below with reference to FIGS. 7 and 8, so as to constitute an inlet valve.

FIG. 5 shows a second aspect of the fluid-flow device of the present invention corresponding to a member 400 for detecting liquid pressure and suitable for forming part of a more complex fluid-flow device that is also capable of incorporating the above-described liquid inlet control member 100.

This liquid pressure detection member 400 comprises a glass closure wafer 20 placed over a stack 30 which has previously been machined so as to form various functional portions of said liquid pressure detection member 400.

This stack 30 comprises a silicon layer 32 surmounting a silicon oxide layer 34, itself placed on a silicon support wafer 36.

This type of stack is commonly referred to as a silicon-on-insulator stack (SOI) and is commercially available in the form of a wafer or a plate of the kind used in particular in the semiconductor electronics industry. As for the liquid inlet control member 100 described above, the roles of these three elements of the stack 30 lead to thicknesses that are significantly different:

- the silicon support wafer 36 acting as a rigid base preferably presents thickness lying in the range 50 $\mu$m to 1000 $\mu$m, and advantageously in the range 300 $\mu$m to 500 $\mu$m;
- the silicon oxide layer 34 is for connecting the silicon support wafer 36 to the silicon layer 32 while keeping a constant spacing between them, while nevertheless being easily removed from certain zones so its thickness must remain very small, preferably in the range 0.1 $\mu$m to 2 $\mu$m, and advantageously in the range 0.5 $\mu$m to 1 $\mu$m; and
- the silicon layer 32 is designed to be machined through a fraction only of its thickness (about half) in order to co-operate with the glass closure wafer 20 to define a cavity and a moving member; this silicon layer 32 which can be made of single-crystal or polycrystalline silicon has initial thickness that preferably lies in the range 1 $\mu$m to 100 $\mu$m, and advantageously in the range 10 $\mu$m to 50 $\mu$m.

The stack 30 is machined using conventional techniques of photolithography and chemical etching in order to obtain the various functional elements of said liquid pressure detector member 400, and in particular a cavity 38 and moving member 40, prior to making the connection between the glass closure wafer 20 and said stack 30. This connection between the closure wafer 20 and the free face of the silicon layer 32 is made in conventional manner by wafer bonding (anodic bonding when the closure wafer is made of glass), after which fixing is obtained in the form of a leaktight connection.

This liquid pressure detector member 400 has a cavity 38 in which a fluid flows, with the flow direction being represented by two horizontal arrows in FIG. 5. Under the pressure of this liquid, the moving member 40 is capable of moving vertically towards or away from the silicon support wafer 36 (double-headed vertical arrow) until it comes into contact with said silicon support wafer 36.

By way of example, the liquid flows through the cavity 38 from an inlet 402 situated to the left of FIG. 5 to an outlet 404 situated to the right of FIG. 5.

In order to remove the material corresponding to the zone 35 of the silicon oxide layer 34, a series of circular section ducts 412 is formed through the entire thickness of the silicon support wafer 36 in register with said zone 35 and the moving member 40.

As can be seen in FIGS. 5A and 5B, these ducts 412 are situated at equal distances apart from one another in register with the entire zone 35 from which silicon oxide is removed from the layer 34.

Another duct 412' of cross-section in the form of a cylindrical wall, preferably an annular wall, is formed throughout the thickness of the silicon support wafer 36 and surrounds the series of ducts 412. This duct 412' serves to separate the remainder of the silicon support wafer 36 from a bearing portion 414 in the form of a cylinder pierced by the ducts 412 situated in register with the moving member 40 and connected to an electrical connection.

In order to hold the bearing portion 414 secure with the stack 30, a fraction 416 of the silicon oxide layer 34 is left intact on the edge of the bearing portion 414 beside the duct 412'. This fraction 416 connects the bearing portion 414 of the silicon layer 32 surrounding the moving member 40, and thus constituting connection means.

In the variant embodiment shown in FIG. 5A, the duct 412' and the fraction 416 are in the form of circularly cylindrical wall segments, whereas the ducts 412 are regularly distributed over a zone of circular shape.

In the variant embodiment shown in FIG. 5B, the ducts 412 are regularly distributed over a zone of rectangular shape, the fraction 416 is constituted by two fractions of semicircular shape situated along two opposite sides of the above-specified rectangle so as to form two "lugs". In FIG. 5B, the duct 412' surrounds both the above-specified zone of rectangular shape and the two fractions 416, said duct 412' then being in the form of a wall of a rectangular section cylinder having two lugs, like a kind of four-leaf clover or a Greek cross.

This pressure detector member 400 is shaped in such a manner that when the liquid pressure exceeds a certain threshold in the cavity 38, the moving member 40 passes from its rest position or open position (as shown in FIG. 5) to an active position or closed position in which the moving member 40 comes into contact with the bearing portion 414 of the silicon support wafer 36.

Under such circumstances, contact between the layer 32 (at the location of the moving member 40) and the wafer 36 (at the location of the bearing portion 414), both of which are made of doped silicon forming a semiconductor that acts as an electrical conductor integrated in a capacitive circuit, gives rise to a sudden increase in capacitance between the electrical connections respectively connected to the layer 32 and to the bearing portion 414 of the support wafer 36, and by detecting such a sudden increase in capacitance it is possible to determine whether a predetermined liquid pressure level has been reached in the cavity 38.

Other variant embodiments can be envisaged, in particular the variant whereby two electrodes forming two bearing portions are provided, said electrodes being separated from each other and from the remainder of the wafer 36.

This liquid pressure detector member 400 forms a liquid pressure sensor which operates in capacitive manner. Nevertheless, other types of sensor may be created using the member 400: a tunnel effect sensor; a Schotky contact sensor; an inductive detector; an optical detector (e.g. using a laser diode which observes the bending of the moving member 40); or a strain gauge.

Such a liquid pressure detector member 400 is very useful in a fluid-flow assembly since it makes it possible to detect when a predetermined pressure level has been reached in the cavity 38, as a function of the pressure level which triggers contact between the moving member 40 and the bearing portion 414.

Naturally, this pressure detector 400 is a differential sensor taking as its pressure reference the outside pressure that exists in the ducts 412 and 412' and in the zone 35 where there is no material.

FIG. 6 relates to a second embodiment of the liquid pressure detector member constituting the second aspect of the invention. In this case, the liquid pressure detector member 400''' further comprises, compared with the first embodiment of the liquid pressure detector member shown in FIGS. 5, 5A, and 5B, a second glass wafer 20'.

Thus, in this liquid pressure detector member 400''', the top closure wafer 20 is a first glass closure wafer 20, and the second glass wafer 20' forms a second closure wafer which is fixed to the face of the support wafer 36 opposite from said first closure wafer 20 made of glass.

The support wafer 36 is provided with a duct 422 passing right through it.

In order to offset the electrical contact zone giving rise to the pressure threshold being detected so that it is shifted towards the second closure wafer 20' made of glass, in the second embodiment of the liquid pressure detector member 400''', the portion forming an island separated from the remainder of the support wafer 36 constitutes a moving portion 461.

The duct 422 is annular so as to separate the moving portion 461 from the remainder of the support wafer 36 and the layer of insulating material 34 presents a connection zone 321 surrounded by the zone 35 connecting said moving portion 461 integrally with said moving member 40.

In order to perform the functions of a pressure detector, this liquid pressure detector member 400''' further comprises a first conductor element 463 situated on the face of said moving portion 461 that faces the second closure wafer 20' of glass and a second conductor element 465 situated on the face of the second closure wafer 20' of glass placed in register with said moving portion 461. Naturally, said first and second conductor elements 463, 465 are suitable for coming into electrical contact when said moving member 40 and said moving portion 461 which is secured thereto come close to the second closure wafer 20' made of glass.

As an alternative to this electrical contact, other detection methods can be used: measurement can be capacitive, inductive, optical, or by strain gauges placed on the moving member 40. In these other cases, the presence and/or location of the first conductor element 463 and/or of the second conductor element 465 needs to be adapted to the detection technique used.

As with the pressure detector 400 described with reference to FIGS. 5, 5A, and 5B, the liquid pressure detector 400''' makes it possible to identify a determined pressure threshold relative to the outside pressure because of the increasing deformation of the moving member 40 due to the increase in the liquid pressure inside the pumping chamber.

Thus, the second embodiment of the pressure detector member as shown in FIG. 6 belongs to a second type of fluid-flow device in which a second glass wafer 20' is necessary in order to be able to offset electrical contact between said second glass wafer 20' and a moving portion 461 of the moving wafer 36 of the stack 30.

The pressure detector and control members 400 and 400''' described above can be integrated in a micropump of the kind described below with reference to FIGS. 7 and 8, as an inlet valve.

Compared with the method of manufacturing the pressure detection control member 400 of the first embodiment (FIGS. 5, 5A, and 5B), in order to manufacture the pressure detection control member 400''' it suffices to provide a second closure wafer 20' on which a second conductor element 465 of electrically conductive material is deposited, and to connect it to the silicon support wafer 36. These two steps are performed at the end of the manufacturing process, i.e. after treating (in particular by machining and/or structuring) the stack 30 and after providing the face of the moving portion 461 facing away from the moving member 40 with a first conductor element 463 made of an electrically conductive material. Naturally, provision must be made to connect the first and second electrically conductive elements 463 and 465 to the circuit of the detector system.

It should be observed that the term "duct" is used for the channels or volumes 412, 412', and 422 in the two embodiments 400 and 400''' of the pressure detector, even though they are not designed to have fluid flowing through them while this fluid-flow member is in operation.

The first and second aspects of the fluid-flow device of the present invention as described above with reference to FIGS. 1 to 6 implement different functions relating to the passing of liquid in a fluid-flow device and are of analogous simple structure suitable for being implemented using a manufacturing method that is very simple to implement.

In addition, this method of manufacturing the various members 100, 100'', 100''', 400 and 400''' as described above presents high degrees of similarity such that these various fluid-flow members 100, 100'', 100''', 400, and 400''' can easily be located in a single fluid-flow assembly.

An example of such integration is described below with reference to FIGS. 7 to 15. The common steps of the method of manufacturing the members 100, 100'', 100''', 400, and 400''' are stated at the beginning of the present description when specifying a method of manufacturing a fluid-flow device, which method presents adaptations in order to make each specific member 100, 100'', 100''', 400, and 400''', as specified below.

The method of manufacturing the liquid inlet control member 100 as shown in FIG. 1 comprises the following steps:

a) a stack 30 is provided that comprises a support wafer 36, preferably made of silicon, a silicon oxide layer 34 covering at least part of the support wafer 36, and a layer of (single-crystal or polycrystalline) silicon 32 covering the silicon oxide layer 34 and presenting a free face opposite from its face covering said layer 34 of silicon oxide;

b) the cavity 38 is machined from the free face of the silicon layer 32 by photolithography and chemical etching;

c) the gap 104 is machined from the free face of the silicon layer 32 by photolithography and chemical etching through the entire thickness of the silicon layer 32 until the layer 34 of silicon oxide is reached;

d) from the other side of the stack 30, the liquid inlet duct 102 passing right through the support wafer 36 is machined by photolithography and chemical etching;

e) the silicon oxide layer 34 is chemically etched through the duct 102 and the gap 104 so as to create the zone 35 that is free from material in the silicon oxide layer 34 so that the zone of the silicon layer 32 situated facing said zone 35 is freed of the layer 34 of silicon oxide, thus forming the moving member 40, which member remains connected to the silicon layer 32 by the arm(s) 41;

f) the closure wafer 20 is provided; and g) physicochemical means are used to connect the closure wafer 20 in leaktight manner to the surface of the silicon layer 32 that has not been subjected to machining, preferably by a wafer bonding technique.

When the closure wafer 20 is made of glass, the above-mentioned wafer bonding technique consists in anodic bonding. If the closure wafer is made of silicon, then direct bonding enables a leaktight connection to be made with the silicon layer 32.

It will thus be understood that the micromachining processing of the stack 30 is performed in independent manner for each of its faces such that the group of steps b) and c), and the group of steps d) and e) can be performed one before the other as described above, or one after the other.

The liquid pressure detector member 400 shown in FIG. 5 and representing the second aspect of the present invention is made using a method that comprises the following steps:

a) a stack 30 is provided comprising a support wafer 36 that is preferably made of silicon, a silicon oxide layer 34 covering at least part of the support wafer 36, and a layer 32 of (single-crystal or polycrystalline) silicon covering the layer 34 and presenting a free face opposite from a face covering the silicon oxide layer 34;

b) a cavity 38 is machined from the free face of the silicon layer 32 by photolithography and chemical etching;

c) from the other side of the stack 30, the ducts 412 and 412' passing right through the support wafer 36 are machined from the other side of the stack 30;

d) the silicon oxide layer 34 is subjected to chemical etching via the ducts 412 and 412' so as to form the zone 35 in the silicon oxide layer 34 that is free from material, while leaving silicon oxide in the fraction 416 so as to release the moving member 40 from the silicon oxide layer 34;

e) the closure wafer 20 is provided; and f) a physicochemical method is used for connecting the closure wafer 20 in leaktight manner to the surface of the silicon layer 32 that has not been subjected to machining, preferably using a wafer bonding technique.

Whether for one of the liquid inlet control members 100, 100", 100''', or for one of the liquid pressure detection members 400, 400''', it will be understood that the machining of the cavity 38 situated between the silicon layer 32 and the closure wafer 20 can be performed equally well by machining the layer 32 and the wafer 20 or by machining the wafer 20 alone.

Reference is now made to FIGS. 7 to 9 showing a micropump 500 forming a fluid-flow assembly integrating a liquid inlet control member 100, a pumping portion 502, a pressure detection member 400, and a liquid outlet control member 200.

Preferably, in addition to the glass closure wafer 20 and the stack 30, the micropump is provided with an additional glass closure wafer 20' bonded to the face of the support wafer 36 opposite from its face carrying the glass closure wafer 20, i.e. in the bottom portions of FIGS. 7 and 8.

It will thus be understood that the closure wafer 20 constitutes a first glass closure wafer and that the additional closure wafer 20' constitutes a second glass closure wafer fixed on the face of the support wafer 36 that is opposite from the face carrying the first glass closure wafer 20.

As described in greater detail below, the glass closure wafer 20 serves not only to close the liquid-filled space of the micropump in leaktight manner, but also as an abutment during the up stroke of the pump diaphragm 506. In order to prevent sticking or a suction cup effect between the pump diaphragm and the closure wafer 20, elements 510 made of an anti-adhesion material are situated on the face 20a of the closure wafer 20 that faces towards the stack.

These elements 510 are preferably derived from a layer of titanium placed on the above-specified face 20a of the closure wafer 20. These elements 510 form mutually separate projections which enable liquid to flow between them while preventing the pump diaphragm 506 from adhering to the closure wafer 20.

It should be observed that these elements 510 could equally well be situated on the silicon layer 32, i.e. in particular on the free face of the diaphragm 506.

The closure wafer 20' also serves as an abutment element, in this case for the down stroke of the diaphragm 506 by contact being established between the wafer 20' and the moving pump portion 514. Combining these two abutments (wafers 20 and 20') makes it possible to control the vertical stroke amplitude of the diaphragm 506 and to ensure that the volume pumped is accurate.

In order to ensure that the part 514 remains free to move, an anti-adhesion layer 520 is provided (see FIGS. 7 and 8) on the additional closure wafer 20' facing towards the stack 30. This layer 520 is in the form of a ring and is positioned on the edge of an opening 522 passing through the additional closure wafer 20'.

The layer 520 is preferably made of titanium and thus prevents the moving pump part 514 from sticking to the additional closure wafer 20' while the stack 30 is being bonded to the additional closure wafer 20'.

Naturally, the layer 520 could equally well be deposited on the face of the moving pump part 514 that faces away from the stack 30.

For the elements 110, 510, and 520, titanium can advantageously be replaced by some other anti-adhesion material such as gold, silicon oxide, or silicon nitride.

In the upstream portion of the micropump 500, there can be found the liquid inlet control member 100, the liquid inlet duct 102 being extended through the additional closure wafer 20' of glass by a liquid inlet duct 102' having an inlet where the liquid that is to be delivered by the micropump 500 arrives.

This liquid inlet control member 100 comprises a zone $35_1$ of the silicon oxide layer 34 that is free from material, the cavity $38_1$, and the gap 104 which define the moving member $40_1$. The liquid inlet control member 100 is shown in its rest position in FIGS. 7 and 8.

Between the liquid inlet control member 100 and a pressure detector 400, the micropump 500 comprises the pumping portion 502 provided with a pump chamber 504 situated in the extension to the cavity $38_1$ and defined between the glass closure wafer 20 and the silicon layer 32 whose face facing towards the glass closure wafer 20 has been machined.

A pump diaphragm 506 in the form of a disk is situated in the silicon layer 32 in register firstly with the pump chamber 504 and secondly with an annular volume 508 that is free from material machined in the support wafer 36, said annular volume 508 free from material being extended in the silicon layer 34 by a material-free zone 535.

This volume 508 serves to separate the remainder of the silicon support wafer 36 from a moving pump part 514 in the form of a solid cylinder of circular section situated in register with the pump diaphragm 506 to which it is connected by a fraction 516 of the silicon oxide layer 34 that has been left intact.

Since the volume 508 is isolated from the remainder of the support wafer 36, it is possible advantageously to integrate in the moving pump part 514 at least one liquid pressure detection member, e.g. in the form of one or more liquid pressure detectors operating in similar manner to that of FIGS. 5, 5A, and 5B.

Such a variant embodiment is shown in FIG. 16A which shows a pumping portion 502' fitted with eight liquid pressure detectors 400' regularly distributed angularly in a moving pump part 514' pierced right through by eight series of ducts 512'. These eight series of ducts 512' are isolated from one another by a fraction 516' of the silicon oxide layer 34 that is left intact except for respective zones in each of the detectors 400' to interconnect the corresponding series of ducts 512'.

Naturally, a pumping portion 502' could be provided that is fitted with at least two liquid pressure detectors 400' each forming a liquid pressure detection member and regularly spaced apart angularly in said moving pump part 514' which is pierced right through by at least two series of ducts 512'.

Another variant embodiment of the pumping portion is shown in FIG. 16B under numerical reference 502". In this case, the eight series of ducts 512' of FIG. 16A are accompanied by other ducts 512' so that all of these ducts cover an annular zone that is to form a single annular liquid pressure detector 400". In this other variant embodiment, the fraction of the silicon oxide layer 34 that is left intact is restricted to a first annular fraction 516"a situated substantially at the edge of the moving pump part 514' and to a second fraction 516"b situated essentially in the center of the moving pump part 514'.

The moving pump part 514' is also pierced right through, preferably in its center, by a passage 540 suitable for receiving a control rod (not shown) having one end fixed to the diaphragm 506 and having its other end projecting out from the opening 522 to form a handle. This handle allows a user, where necessary, to pull the diaphragm 506 by means of said rod in order to move it away from the closure wafer 20. A series of such actions can be performed to develop high levels of suction in succession in the pump chamber 504, or else to accelerate the operation of the micropump. It should be observed that the presence of the passage 540 and of the rod is independent of the presence of a pressure detection member in the moving pump part 514.

It should also be observed that the micropump control means situated in register with the pump diaphragm 506 and generically referred to as an actuator can be integrated directly in the micropump by being fixed on the face of the glass wafer 20' facing away from the stack and by being fixed to the moving pump part 514, or can be external to the micropump, being connected indirectly to the pump diaphragm 506.

These control means may, in particular, be of the type operating piezoelectrically, electromagnetically, or pneumatically.

Downstream from the pumping portion 502, the micropump 500 shown in FIGS. 7 and 8 includes the liquid pressure detector 400 described with reference to FIGS. 5, 5A, and 5B, the passage 412 being connected to external pressure via a duct 413' passing through the additional glass closure wafer 20'. In addition, there can be seen the other component elements of the liquid pressure detection member 400, specifically the zone $35_4$ of the silicon oxide layer 34 that is free from material, and the cavity $38_4$ which defines the moving member $40_4$ between a liquid inlet 402 and a liquid outlet 404.

In FIGS. 7 and 8, the liquid pressure detection member 400 is shown in its rest or open position, i.e. with a moving member $40_4$ that is not in contact with the bearing portion 414. It should be observed that the electrical connections to the bearing portion 414 and to the silicon layer 32 are not shown.

It will thus be understood that the pressure detector servers to verify that the micropump is operating properly by detecting the transient increase in liquid pressure on each stroke of the pump that results from the pump diaphragm 506 deflecting (an increase in pressure corresponding to the diaphragm 506 moving upwards in FIGS. 7 and 8, and vice versa). It is possible to detect either that pumping is not taking place because there is no increase in pressure, or else that there is a blockage downstream because of the high pressure lasting for an excessively long period of time.

In the furthest downstream portion of the micropump 500, there is a liquid outlet control member 200 shown on a larger scale in FIG. 17.

This liquid outlet control member 200 forms a non-return check valve through which the liquid is delivered via a liquid outlet duct 204 through the silicon support wafer 36 and extended through the additional glass closure wafer 20' by a liquid outlet duct 204'.

The other component elements of this liquid outlet control member 200 are a zone $35_2$ that is free from material in the silicon oxide layer 34, a moving member $40_2$ defined by the cavity $38_2$, said moving member $40_2$ having an annular fraction 206 forming the valve body with the second end thereof coming into contact with an anti-adhesive layer 210 situated on the closure wafer 20, the annular fraction 206 being pieced by an orifice 208. In FIGS. 7 and 8, the outlet control member 200 is shown in the closed position.

The liquid outlet control member 200 shown on a larger scale in FIG. 17, and its variant embodiment 300 shown in FIG. 18 are made using the same elements as the member 100 of FIG. 1.

As can be seen in FIG. 17, the liquid outlet control member 200 presents a liquid inlet 202 in the cavity $38_2$ and a liquid outlet duct 204 machined through the entire thickness of the silicon support stack 36 in register with the cavity 38.

The zone $35_2$ of the silicon oxide layer 34 that is free from material is located at least in line with the liquid outlet duct 204 and extends slightly beyond it all around said duct 204.

When making the cavity 38 by machining the silicon layer 32, the moving member 40 is formed with a fraction 206 extending over substantially the entire initial thickness of the silicon layer 32 and presenting a closed outline, preferably an annular outline. This fraction 206 extends from a first end 206a facing the zone $35_2$ of the layer of insulating material 34 to a second end 206b close to the face 20a of the closure wafer 20 facing towards the stack 30.

This fraction 206 is in the form of a preferably annular cylindrical sleeve and it surrounds an orifice 208 situated in line with the zone $35_2$ and the duct 204 with which the orifice 208 is in fluid communication.

In this liquid outlet control member 200, the moving member 40 lies across substantially the entire section of the liquid outlet duct 204.

The valve seat is constituted by an anti-adhesion element 210, preferably made of titanium, situated on the face 20a of the glass closure wafer 20 facing towards the moving member $40_2$. This anti-adhesion element 210 is similar in shape to the fraction 206, and is thus preferably annular. This anti-adhesion element 210 could also be situated on the second end 206b of the fraction 206 and could equally well be made of some other anti-adhesion material such as gold, silicon oxide, or silicon nitride.

The valve body is constituted by the second end 206b of the annular fraction 206 whose first end 206a faces towards the silicon support wafer 36 and is adjacent to the liquid outlet duct 204.

In order to minimize the contact areas of the valve, the second end 206b of the annular fraction 206 is of small thickness, the orifice 208 being larger at this level.

In FIG. 17, the liquid outlet control member 200 is shown in the rest position corresponding to a closed position, the liquid arriving via the inlet 202 being prevented from penetrating into the orifice 208 by the fraction 206 whose second end 206b is in leaktight contact with said anti-adhesion element 210.

Sufficient liquid pressure in the liquid inlet 202 exerts force on the moving member making it possible, if the liquid pressure in the outlet duct 204 is less than the liquid inlet pressure, to open the valve by moving the moving member $40_2$ towards the silicon support wafer 36 (configuration not shown). In this open position, the liquid can pass over the second end 206b of the fraction 206 which has been moved away from said anti-adhesion element 210 and the closure wafer 20, so as to penetrate into the orifice 208 which is in direct fluid communication with the liquid outlet duct 204.

It will also be understood that said anti-adhesion element 210 makes it possible to prevent the valve body formed by the second end 206b of the fraction 206 sticking against the valve seat (the face of said anti-adhesion element 210 that faces towards the stack 30).

In addition, it will be understood that said anti-adhesion element 210 makes it possible by an initial elastic displacement of the moving member $40_2$ to establish pretension in the liquid outlet control member 200 so that the valve remains closed in its rest position and for liquid pressure that does not exceed a predetermined threshold.

It is also by means of a resilient return phenomenon whereby, when the liquid pressure in the inlet 202 is less than or equal to the liquid pressure in the outlet duct 204, the control member 200 returns to its closed position shown in FIG. 17, the leaktight contact between the second end 206b of the fraction 206 and said anti-adhesion element 210 preventing any subsequent flow of liquid from the liquid inlet 202 to the orifice 208.

FIG. 18 shows a variant embodiment corresponding to a liquid outlet control member 300 in which the liquid inlet 302 is made in the cavity 38 while the liquid outlet duct 304 passes right through the glass closure wafer 20.

The moving member 40 of this liquid outlet control member 300 is very similar in shape to the moving member 40 of FIG. 17: it has an annular fraction 306 similar to the fraction 206, however it does not have an orifice such as the orifice 208.

In this case, the annular fraction 306 still acts as the valve body by making leaktight contact (in the closed position as shown in FIG. 18) between the second end 306b of the annular fraction 306 facing towards the closure wafer and facing an anti-adhesion element 310 that itself faces the stack 30.

In this case, in order to enable the moving member 40 to move vertically, as represented by the double-headed arrow in FIG. 18, the zone 35 of the silicon oxide layer 34 that is free of material extends in register with all the moving member 40.

In addition, access to the silicon oxide layer 34 is provided from the free face of the silicon support stack 36 in order to remove silicon oxide from the zone 35 by means of a passage 312 that passes right through the silicon support stack 36. This passage 312 preferably, but not necessarily, presents a cylindrical shape, being circular in cross-section as shown in FIG. 18.

The micropump 500 can be used in numerous applications, in particular as a pump for medical use for continuously delivering a liquid medicine.

Because of its very small dimensions, such a pump may be of the "implantable" type, i.e. it may be placed beneath the skin of a patient, or it may be of the external type, and be connected via its inlet control member 100 to the patient's blood circulation system via an inlet port passing through the skin.

FIGS. 10 to 15 show various steps in manufacturing the micropump 500 comprising in particular steps of manufacturing the members 100, 200, and 400, and the pumping portion 502, these steps being performed simultaneously.

In these various manufacturing steps, a distinction is drawn between "machining" which is used for machining that is intended to vary the thickness of a wafer or certain zones of a wafer, and the term "structuring" which is used for machining in the sense of conserving the material of a layer in certain zones and removing all of the material of that layer from other zones.

Figure 11:
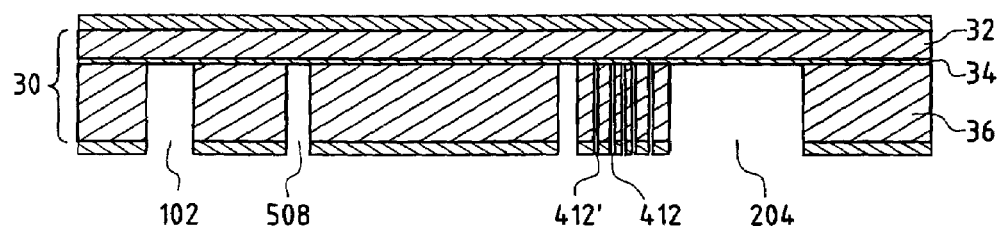
Figure 12:
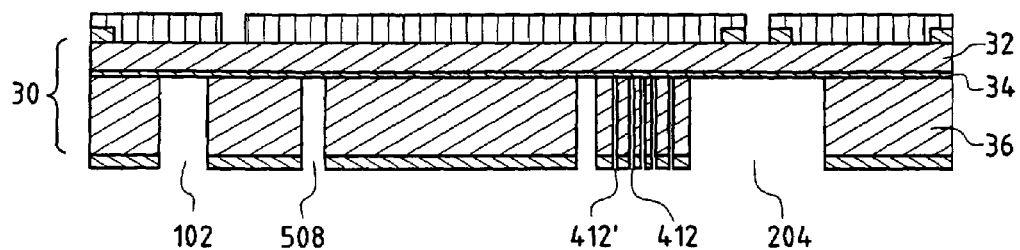
Figure 13:
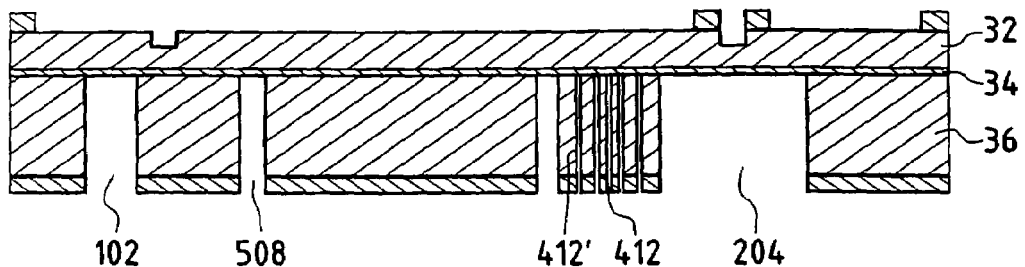
Figure 14:
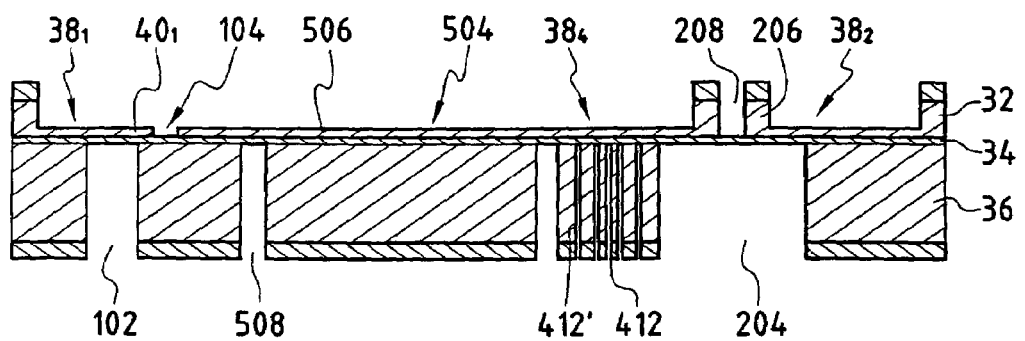
Figure 15:
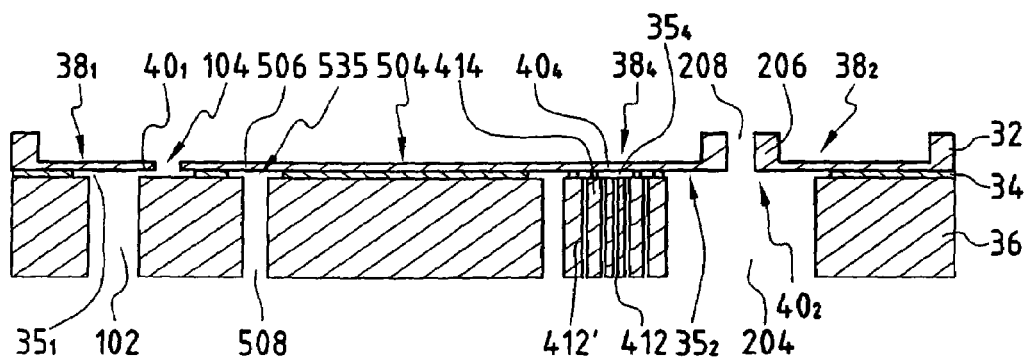

The method of manufacturing the micropump 500 comprises the following steps:

a) a stack 30 is provided comprising a support wafer 36 preferably made of silicon, a layer of insulating material 34 preferably made of silicon oxide and covering at least part of the support wafer 36, and a layer 32 of (single-crystal or polycrystalline) silicon covering the layer 34 of insulating material and presenting a free face opposite from a face covering the layer 34 of insulating material;

b) by means of photolithography and chemical etching from the free face of the support wafer 36, the following are machined: the liquid inlet duct 102 of the inlet control member 100, the annular volume 508, the ducts 412 and 412' of the pressure detector 400, and the liquid outlet duct of the liquid outlet control member 200, these ducts or annular volume passing right through the support wafer 36 (FIG. 11);

c) by means of photolithography and chemical etching (hydrofluoric acid or BHF-buffered hydrofluoric acid) from the other side of the stack 30, i.e. from the free face of the silicon layer 32, the following are machined: the gap 104 and the cavity $38_1$ of the inlet control member 100, the pump chamber 504, the cavity $38_4$ of the pressure detector 400, the cavity $38_2$, and the orifice 308 of the liquid outlet control member 200 (FIGS. 9 to 14);

d) the silicon oxide layer 34 is subjected to chemical etching via the liquid inlet duct 102 of the inlet control member 100, via the annular volume 508, via the ducts 412 and 412' of the pressure detector 400, and via the liquid outlet duct 204 of the liquid outlet control member 200 so as to form the zones $35_1$, 535, $35_4$ and $35_2$ of the silicon oxide layer 34 that are free from material, thus making it possible to release the following respectively from the silicon oxide layer 34: the moving member $40_1$, the diaphragm 506, the moving member $40_4$, and the moving member $40_2$ (FIG. 15);

e) the first closure wafer 20 is provided; and f) a layer of anti-adhesion material, preferably titanium, is deposited by a physicochemical method on a face 20a of the first closure wafer 20 that is to be connected to said stack 30;

g) the layer of anti-adhesion material is structured as to form said elements 510 and said anti-adhesion layer 210;

h) the second closure wafer 20' is provided;

i) a layer of anti-adhesion material, preferably titanium, is deposited by a physicochemical method on a face of the second closure wafer 20' that is to be connected to said stack 30;

j) the layer of anti-adhesion material is structured so as to form said ring-shaped layer 520;

k) the first closure wafer 20 is connected in leaktight manner by a physicochemical method to the surface of the silicon layer 32 which has not been machined, preferably by wafer bonding; and l) the second closure wafer 20' is connected in leaktight manner by a physicochemical method to the surface of the support wafer 36 that has not been machined, preferably by wafer bonding.

It will be understood that the micropump 500 as obtained in this way is manufactured in a manner that is very simple and that presents very regular thickness characteristics for all of its component portions because they are made from the same initial stack 30, thereby guaranteeing in particular that the pumping dead volume is very small.

As an illustration of the simplification provided by the manufacturing method, in order to make a prior art micropump it is necessary to use about twelve photolithographic masks in order to make and machine all of the various layers, whereas using the above-described method of the present invention, about five masks suffices.

The invention claimed is:

1. A method of manufacturing a fluid-flow device, the method comprising the following steps:
   providing a stack (30) comprising a support wafer (36), one layer of insulating material (34) covering directly at least part of said support wafer (36), and one layer of single-crystal or polycrystalline silicon (32); covering directly said layer of insulating material (34) and presenting a free face;
   providing at least one closure wafer (20);
   using photolithography and chemical etching to machine a cavity (38) from said closure wafer (20) and/or from the free face of said silicon layer (32);
   using photolithography and chemical etching to machine at least one duct (102) passing right through said support wafer (36);
   chemically etching said layer of insulating material (34) at least via said duct (102) such that a zone (35) of said silicon layer (32) is freed from said layer of insulating material (34), thereby forming a moving member (40) in said silicon layer (32), said moving member (40) remaining connected to the silicon layer (32) and facing said freed zone (35);
   using a physicochemical method to connect said closure wafer (20) in leaktight manner directly to said free face of silicon layer (32) thereby said moving member (40) facing said cavity (38).

2. Method according to claim 1, wherein said support wafer (36) is made of silicon.

3. Method according to claim 1, wherein said insulating material (34) is made of silicon oxide.

4. Method according to claim 1, wherein said physicochemical method is a wafer bonding technique.

5. A method of manufacturing a liquid inlet control member 100, the method comprising the steps of:
   providing a stack (30) that comprises a support wafer (36), one insulating material layer 34 covering directly at least part of the support wafer (36), and one layer of silicon (32) covering directly the insulating material layer (34) and presenting a gee face opposite from its face covering said layer (34) of insulating material;
   machining a cavity (38) from the free face of the silicon layer (32) by photolithography and chemical etching;
   machining a gap (104) from the free face of the silicon layer (32) by photolithography and chemical etching through the entire thickness of the silicon layer (32) until the layer (34) of insulating material is reached;
   from the other side of the stack (30), machining a liquid inlet duct (102) passing right through the support wafer (36) by photolithography and chemical etching;
   chemically etching the insulating material layer (34) through the duct (102) and the gap (104) so as to create a zone (35) that is freed from material in the insulating material layer (34) so that the zone of the silicon layer (32) situated facing said zone (35) is freed of the layer (34) of insulating material, thus forming the moving member (40) in said silicon layer (32), which moving member (40) remains connected to the silicon layer (32) by arm(s) (41) and faces said freed zone (35);
   providing a closure wafer (20); and
   using physicochemical means to connect the closure wafer (20) in leaktight manner directly to said free face of the silicon layer (32).

6. Method according to claim 5, wherein said support wafer (36) is made of silicon.

7. Method according to claim 5, wherein said insulating material (34) is made of silicon oxide.

8. Method according to claim 5, wherein said physicochemical method is a wafer bonding technique.

9. A method of manufacturing a liquid pressure detector member 400, the method comprising the steps of:
   providing a stack (30) comprising a support wafer (36), one insulating material layer (34) covering directly at least part of the support wafer (36), and one layer (32) of silicon covering directly the insulating material layer (34) and presenting a free face opposite from a face covering the insulating material layer (34);
   machining a cavity (38) from the free face of the silicon layer (32) by photolithography and chemical etching;
   from the other side of the stack (30), machining at least two ducts (412) and (412') passing right through the support wafer (36);
   subjecting the insulating material layer (34) to chemical etching via the ducts (412) and (412') so as to form a zone (35) in the insulating material layer (34) that is free from material, while leaving insulating material in the fraction (416) so as to release a moving member (40) from the insulating material layer (34), said moving member (40) remaining connected to the silicon layer 32 and facing said freed zone;
   providing a closure wafer (20), and
   using a physicochemical method for connecting the closure wafer (20) in leaktight manner directly to said freed face of the silicon layer (32).

10. Method according to claim 9, wherein said support wafer (36) is made of silicon.

11. Method according to claim 9, wherein said insulating material (34) is made of silicon oxide.

12. Method according to claim 9, wherein said physicochemical method is a wafer bonding technique.

13. A method of manufacturing a micropump (500), the method comprising the steps of:
   providing a stack (30) comprising a support wafer (36), one layer of insulating material (34) and covering directly at least part of the support wafer (36), and one layer (32) of silicon covering directly the layer (34) of insulating material and presenting a free face opposite a face covering the layer (34) of insulating material;
   by means of photolithography and chemical etching from the free face of the support wafer (36), machining the following: one liquid inlet duct (102) of the inlet control member (100), an annular volume (508), at least two ducts (412) and (412') of a pressure detector (400), and a liquid outlet duct of a liquid outlet control member (200), these ducts or annular volume passing right through the support wafer (36);
   by means of photolithography and chemical etching, from the other side of the stack (30), that is, from the free face of the silicon layer (32), machining the following: a gap (104) and a first cavity (381) of the inlet control member (100), a pump chamber (504), a second cavity (384) of the pressure detector (400), a third cavity (382), and an orifice (308) of the liquid outlet control member (200);
   subjecting the insulating material layer (34) to chemical etching via the liquid inlet duct (102) of the inlet control member (100), via the annular volume (508), via the ducts (412) and (412') of the pressure detector (400), and via the liquid outlet duct (204) of the liquid outlet control member (200) so as to form zones (351), (535), (354) and (352) of the insulating material layer (34) that are free from material, thus making it possible to release the following moving members respectively from the insulating material layer (34): a first moving member (401), a diaphragm (506), a second moving member (404), and a third moving member (402), said moving members remaining connected to the silicon layer (32) and respectively facing one of freed zones (351), (535), (354) and (352) of the insulating material layer (34);

providing a first closure wafer (20);

depositing a layer of anti-adhesion material by a physicochemical method on a face (20a) of the first closure wafer (20) that is to be connected to said stack (30), the layer of anti-adhesion material being structured as to form elements (510) and an anti-adhesion layer (210);

providing a second closure wafer (20')

depositing another layer of anti-adhesion material by a physicochemical method on a face of the second closure wafer (20') that is to be connected to said stack (30), said layer of anti-adhesion material being structured so as to form a ring-shaped layer (520);

directly connecting the first closure wafer (20) in leaktight manner by a physicochemical method to the free face of the silicon layer (32); and connecting the second closure wafer (20') in leaktight manner by a physicochemical method to the surface of the support wafer (36) that is not covered by the layer of insulating material (34).

14. Method according to claim 13, wherein said support wafer (36) is made of silicon.

15. Method according to claim 13, wherein said insulating material (34) is made of silicon oxide.

16. Method according to claim 13, wherein said physicochemical method is a wafer bonding technique.

17. Method according to claim 13, wherein said anti-adhesion material is made of titanium.

* * * * *